(12) United States Patent
Lima Aragão et al.

(10) Patent No.: US 12,310,308 B2
(45) Date of Patent: May 27, 2025

(54) METHOD FOR OBTAINING RICIN/RCA-FREE CASTOR-OIL PLANT SEEDS, RICIN/RCA-FREE CASTOR-OIL PLANTS, METHOD FOR IDENTIFYING RICIN/RCA-FREE CASTOR-OIL PLANTS, POLYNUCLEOTIDES, CONSTRUCTS AND USES THEREOF

(71) Applicants: EMPRESA BRASILEIRA DE PESQUISA AGROPECUÁRIA—EMBRAPA, Brasília (BR); FUNDAÇÃO UNIVERSIDADE DE BRASÍLIA, Brasília (BR)

(72) Inventors: Francisco José Lima Aragão, Brasilia (BR); Glaucia Barbosa Cabral, Brasilia (BR); Aisy Botega Baldoni Tardin, Brasilia (BR); Natalia Lima De Sousa, Brasilia (BR)

(73) Assignees: EMPRESA BRASILEIRA DE PESQUISA AGROPECUÁRIA—EMBRAPA, Brasília (BR); FUNDAÇÃO UNIVERSIDADE DE BRASÍLIA, Brasília (BR)

( * ) Notice: Subject to any disclaimer, the term of this patent is extended or adjusted under 35 U.S.C. 154(b) by 269 days.

(21) Appl. No.: 17/292,307

(22) PCT Filed: Nov. 6, 2019

(86) PCT No.: PCT/BR2019/050480
§ 371 (c)(1),
(2) Date: May 7, 2021

(87) PCT Pub. No.: WO2020/093128
PCT Pub. Date: May 14, 2020

(65) Prior Publication Data
US 2021/0395764 A1    Dec. 23, 2021

(30) Foreign Application Priority Data
Nov. 9, 2018    (BR) .......................... 102018073082-7

(51) Int. Cl.
*A01H 6/38*        (2018.01)
*C12N 15/82*       (2006.01)

(52) U.S. Cl.
CPC ........... *A01H 6/38* (2018.05); *C12N 15/8247* (2013.01)

(58) Field of Classification Search
None
See application file for complete search history.

(56) References Cited

U.S. PATENT DOCUMENTS

| 6,620,986 B1 * | 9/2003 | McKeon | ............ C12N 15/8205 800/294 |
| 2009/0077656 A1 * | 3/2009 | Oka | ..................... H04N 1/4413 726/21 |

OTHER PUBLICATIONS

Sousa et al. 2017, Scientific Reports, 7:15385.*
GenBank DQ661048.1., submitted May 31, 2006.*
Barnes, Daniel Joseph, "An approach to genetic silencing of Ricin in Castor (*Ricinus communis* L)" (2014. Theses and Dissertation, 478 (Mississippi State University).*
El-Nikhely N, Helmy M, Saeed LA, Shama A, and El_Rahman A. Protein J. 2007, 26:481-489).*
Sousa et al 2017. Scientific Reports, 7: 15385, DOI: 10.1038/s41598-017-15636-7.*
Sousa et al., "Bio-detoxification of ricin in castor bean (*Ricinus communis* L.) seeds", Scientific Reports, vol. 7, No. 15385, 2017, pp. 1-9.
Baldoni, "Ricin accumulation in castor bean seeds and gene silencing in genetically modified plants", University of Brasilia Institute of Biological Sciences Department of Cellular Biology Post-Graduation in Molecular Biology, 2010, pp, i-xi, 1-71 (126 pages total).
Nikhely et al., "*Ricinus communis* ricin A chain gene, partial cds", GenBank: DQ661048.1, Jul. 2016, 1 page.
Wesley et al., "Cloning vector pKANNIBAL", GenBank: AJ311873. 1, Nov. 2006, 3 pages.
Sousa, "Development of Systems to the Castor Plant (*Ricinus communis* L.) Gene Transformation—The Bases for Ricin Silencing", University of Brasilia Institute of Biological Sciences Department of Botany Post-Graduation Program in Botany, 2013, 106 pages total.

(Continued)

*Primary Examiner* — Cynthia E Collins
(74) *Attorney, Agent, or Firm* — Sughrue Mion, PLLC

(57) ABSTRACT

This invention relates to a method for obtaining castor-oil plants deprived of the ricin/RCA protein, through the insertion of gene constructs into plant cells, particularly castor-oil plant ones, with the consequent production of ricin/RCA-free castor-oil plant seeds. An aspect of the invention consists in providing castor-oil plants and parts thereof containing said gene construct. The method disclosed herein appeared to be efficient to the generation of castor-oil plants deprived of ricin protein or showing low expression levels of this protein, thus allowing the use of the seed thereof to the production of detoxified cakes, both for animal nutrition and for fertilizers, not to mention its possible production in countries that set restrictions to this substance, due to ricin toxicity. Therefore, this invention also provides a method and a kit to the identification of transformed plants containing the gene constructs disclosed herein.

2 Claims, 9 Drawing Sheets

Specification includes a Sequence Listing.

(56) References Cited

OTHER PUBLICATIONS

Sousa, "Bio-Detoxification of Castor Plant Seeds (*Ricinus communis* I) by Silencing the Ricin Gene", Biotechnology and Biodiversity PhD Program, University of Brasília, Dec. 2017, pp. cover, i-x, 11-76 (106 pages).
Baldoni et al., "Immunolocalization of ricin accumulation during castor bean (*Ricinus communis* L.) seed development", International Journal of Plant Biology 2010; vol. 1, No. e12, pp. 61-65 ( 6 pages).
International Search Report dated Feb. 4, 2020 from the International Searching Authority in International Application No. PCT/BR2019/050480.
Written Opinion dated Feb. 4, 2020 from the International Searching Authority in International Application No. PCT/BR2019/050480.
Sousa, "Development of Systems for Genetic Transformation of Castor Bean Seeds (*Ricinus communis* L.)—The Basis for the Silence of Ricina", University of Brasilia Institute of Biological Sciences Botanical Department Postgraduate Program in Botanical, 2013, 64 pages.
Sousa, "Bio-detoxification of castor bean seeds (*Ricinus communis* L.) by silencing the ricin gene", Biotechnology and Biodiversity PhD Program, University of Brasília, Dec. 2017, pp. cover, i-x, 11-76 (77 pages).

* cited by examiner

Ricin gene transcript siRNA

- 25 nt
- 18 nt

Loading control

Δricin [gel image with lanes labeled TB14S-5D, NT, pRicRNAi]

FIGURE 7

```
SEQUENCE LISTING

<160> NUMBER OF SEQ ID NOS: 27

<210> SEQ ID NO 1
<211> LENGTH: 2483
<212> TYPE: DNA
<213> ORGANISM: Arabidopsis thaliana

<400> SEQUENCE: 1
tctagattat gtatttccaa ctttcattaa caatataatc gcatataaat gaaaaatcgt      60
ttccaggata atattttgat gaaatctcat attattgttc gtactcggat tgatgttgaa     120
ggcttgaagc gcttcaaatt atagaccaga ttatttaagt ttttcttttg tttactccat     180
atcaatttga tccattatac tacctaagaa aatttaggta acatagaatt atttattgtt     240
atagtaaaaa aaaggaaaac cacaaaaata atctactttt acgtatatac tattttcatg     300
acataagtaa ttaagttgta caactttttt ttaatgaaaa gagagagtaa atttatcatg     360
ttcatgtgta gttacctcgt gaataaccga cggttatata gacgcctaac atgaattgtt     420
cagttgaaga cagttcaaaa catgtgtttc actctaaaat cctcaacaaa aaaaagtgt      480 taaaatttgt aaacctcttt caagcaaaaa aagaaaaagt gttagaatcc caagattctt     540
tcataatccg gaatcttggc tgaaaacgta taaagagat tgacgtagta acaaggagtc      600
ttggtatgct tccatgcttt ttatccttt ttgtcatgga accatgattt ggttaccatt      660
tattatgtaa ccgaaatttt cattgtaata atgaatattt aaattttag caaaaaaaa       720 caaaaaaaaa caaggagtct tgtcttcgtt ctcaaatttc agagctcttg cactttcaa      780 gagttttact ttgatgagtg agacatttgt cttttagtg tttattttct aaacttaaaa      840
tagtagcatc aacatcactc aattataatt cttaagatgt tgtagaaaaa tattttatag     900
atggaaagta atcgatatta agacaaataa gaaaccaaac cggactttgt gttcagaccg     960
aatcaaatct gaattggaga aattatggtg gaggcgaaag tcaacggaac taaagtataa    1020
aaccaaatgt caaaaataaa acccaatttt catccttaaa cgaacctgct gaaaccctaa    1080
tttcgattac caattccgat ctaaaagaa gtcatggaag ccattgattc cgcaatcgat    1140
cctctcagag atttcgctaa gagcagtgtt cgtctcgtcc agcgctgtca caaacccgat    1200
cgcaagggta acgcctttc tcaaaaaaat ctcatttccg attttgatc tgtagattag     1260
```

```
ggttttctga aattttgata tcatttgtaa ttgaattggt tatcagaatt cacgaaagta    1320
gctgtgcgta cggcgattgg atttgtggtg atgggattcg ttggattctt cgtgaagctc    1380
gttttcatcc caatcaacaa catcatcgtt ggatcttctt agtgtagtac tttctttacg    1440
aggtaattga tctcgcatta tatatctaca ttttggttat gttacttgac atatagtcat    1500
tgattcaata gttctgttaa ttcctttaaa gatcattttg actagaccac attcttggtt    1560
cattcctcaa taatttgtaa tcatattggt ggatatagaa gtagattggt tatagatcag    1620
atagtggaag actttaggat gaatttcagc tagtttttt ttttggctta ttgtctcaaa    1680
agattagtgc tttgctgtct ccattgcttc tgctatcgac acgcttctgt ctccttgtat    1740
ctttattata tctattcgtc ccatgagttt tgtttgttct gtattcgttc gctctggtgt    1800
catggatgga gtctctgttc catgtttctg taatgcatgt tgggttgttt catgcaagaa    1860
atgctgagat aaacactcat tgtgaaagt ttctaaactc tgaatcgcgc tacaggcaat    1920
gctccgagga gtaggaggag aagaacgaac caaacgacat tatcagccct ttgaggaagc    1980
tcttagtttt gttattgttt ttgtagccaa attctccatt cttattccat tttcacttat    2040
ctcttgttcc ttatagacct tataagtttt ttattcatgt atacaaatta tattgtcatc    2100
aagaagtatc tttaaaatct aaatctcaaa tcaccaggac tatgttttg tccaattcgt    2160 ggaaccaact tgcagcttgt atccattctc ttaaccaata aaaaagaaa gaaagatcaa    2220 tttgataaat ttctcagcca caattctac atttaggttt tagcatatcg aaggctcaat    2280
cacaaataca atagatagac tagagattcc agcgtcacgt gagttttatc tataaataaa    2340
ggaccaaaaa tcaaatcccg agggcatttt cgtaatccaa cataaaaccc ttaaacttca    2400
agtctcattt ttaaacaaat catgttcaca agtctcttct tcttctctgt ttctctatct    2460
cttgctcatc tttctcctga acc                                           2483
```

```
<210> SEQ ID NO 2
<211> LENGTH: 2014
<212> TYPE: DNA
<213> ORGANISM: Arabidopsis thaliana

<400> SEQUENCE: 2
atggcggcgg caacaacaac aacaacaaca tcttcttcga tctccttctc caccaaacca      60
tctccttcct cctccaaatc accattacca atctcccagat tctccctccc attcccccta    120
aaccccaaca atcatcctc ctcctcccgc cgccgcggta tcaaatccag ctctccctcc     180
tccatctccg ccgtgctcaa cacaaccacc aatgtcacaa ccactccctc tccaaccaaa    240
cctaccaaac ccgaaacatt catctcccga ttcgctccag atcaacccgc caaaggcgct    300
gatatcctcg tcgaagcttt agaacgtcaa ggcgtagaaa ccgtattcgc ttaccctgga    360
ggtgcatcaa tggagattca ccaagcctta accgctctct cctcaatccg taacgtcctt    420
cctcgtcacg aacaaggagg tgtattcgca gcagaaggat acgctcgatc ctcaggtaaa    480
ccaggtatct gtatagccac ttcaggtccc ggagctacaa atctcgttag cggattagcc    540
gatgcgttgt tagatagtgt tcctcttgta gcaatcacag gacaagtccc tcgtcgtatg    600
attggtacag atgcgtttca agagactccg attgttgagg taacgcgttc gattacgaag    660
cataactatc ttgtgatgga tgttgaagat atccctagga ttattgagga agctttcttt    720
ttagctactt ctggtagacc tggacctgtt tggttgatg ttcctaaaga tattcaacaa    780
cagcttgcga ttcctaattg ggaacaggct atgagattac ctggttatat gtctaggatg    840
```

```
cctaaacctc cggaagattc tcatttggag cagattgtta ggttgatttc tgagtctaag      900
aagcctgtgt tgtatgttgg tggtggttgt ttgaattcta gcgatgaatt gggtaggttt      960
gttgagctta cggggatccc tgttgcgagt acgttgatgg ggctgggatc ttatccttgt     1020
gatgatgagt tgtcgttaca tatgcttgga atgcatggga ctgtgtatgc aaattacgct     1080
gtggagcata gtgatttgtt gttggcgttt ggggtaaggt ttgatgatcg tgtcacgggt     1140
aagcttgagg cttttgctag tagggctaag attgttcata ttgatattga ctcggctgag     1200
attgggaaga ataagactcc tcatgtgtct gtgtgtggtg atgttaagct ggctttgcaa     1260
gggatgaata aggttcttga gaaccgagcg gaggagctta agcttgattt tggagttttgg    1320
aggaatgagt tgaacgtaca gaaacagaag tttccgttga gctttaagac gtttggggaa     1380
gctattcctc cacagtatgc gattaaggtc cttgatgagt tgactgatgg aaaagccata     1440
ataagtactg gtgtcgggca acatcaaatg tgggcggcgc agttctacaa ttacaagaaa     1500
ccaaggcagt ggctatcatc aggaggcctt ggagctatgg gatttggact tcctgctgcg     1560
attggagcgt ctgttgctaa ccctgatgcg atagttgtgg atattgacgg agatggaagc     1620
tttataatga atgtgcaaga gctagccact attcgtgtag agaatcttcc agtgaaggta     1680
cttttattaa caaccagca tcttggcatg ttatgcaat gggaagatcg gttctacaaa      1740
gctaaccgag ctcacacatt tctcggggat ccggctcagg aggacgagat attcccgaac     1800
atgttgctgt ttgcagcagc ttgcgggatt ccagcggcga gggtgacaaa gaaagcagat     1860
ctccgagaag ctattcagac aatgctggat acaccaggac cttacctgtt ggatgtgatt     1920
tgtccgcacc aagaacatgt gttgccgatg atcccgagtg gtggcacttt caacgatgtc     1980
ataacggaag gagatggccg gattaaatac tgag                                 2014

<210> SEQ ID NO 3
<211> LENGTH: 1221
<212> TYPE: DNA
<213> ORGANISM: Arabidopsis thaliana

<400> SEQUENCE: 3
agatgaaacc ggtgattatc agaaccttt atggtctttg tatgcatatg gtaaaaaaac        60
ttagtttgca atttcctgtt tgttttggta atttgagttt cttttagttg ttgatctgcc      120
tgcttttggg tttacgtcag actactactg ctgttgttgt ttggtttcct ttctttcatt      180
ttataaataa ataatccggt tcggtttact ccttgtgact ggctcagttt ggttattgcg      240
aaatgcgaat ggtaaattga gtaattgaaa ttcgttatta gggttctaag ctgttttaac      300
agtcactggg ttaatatctc tcgaatcttg catggaaaat gctcttacca ttggttttta      360
attgaaatgt gctcatatgg gccgtggttt ccaaattaaa taaaactacg atgtcatcga      420
gaagtaaaat caactgtgtc cacattatca gttttgtgta tacgatgaaa tagggtaatt      480
caaaatctag cttgatatgc cttttggttc attttaacct tctgtaaaca tttttttcaga    540
ttttgaacaa gtaaatccaa aaaaaaaaaa aaaaaatct caactcaaca ctaaattatt      600
ttaatgtata aagatgctt aaaacatttg gcttaaaaga aagaagctaa aaacatagag       660
aactcttgta aattgaagta tgaaaatata ctgaattggg tattatatga atttttctga     720
tttaggattc acatgatcca aaaggaaat ccagaagcac taatcagaca ttggaagtag      780
gaatatttca aaaagttttt tttttttaag taagtgacaa aagcttttaa aaatagaaa     840
agaaactagt attaaagttg taaatttaat aaacaaaaga aatttttat atttttttcat    900
ttcttttttcc agcatgaggt tatgatggca ggatgtggat ttcatttttt tccttttgat    960
```

```
agccttttaa ttgatctatt ataattgacg aaaaaatatt agttaattat agatatattt    1020
taggtagtat tagcaattta cacttccaaa agactatgta agttgtaaat atgatgcgtt    1080
gatctcttca tcattcaatg gttagtcaaa aaaataaaag cttaactagt aaactaaagt    1140
agtcaaaaat tgtactttag tttaaaatat tacatgaata atccaaaacg acatttatgt    1200
gaaacaaaaa caatatctag a                                              1221
```

<210> SEQ ID NO 4
<211> LENGTH: 1337
<212> TYPE: DNA
<213> ORGANISM: Artificial Sequence
<220> FEATURE:
<223> OTHER INFORMATION: Synthetic sequence, 35S promoter of cauliflower mosaic virus

<400> SEQUENCE: 4

```
tcgacgaatt aattccaatc ccacaaaaat ctgagcttaa cagcacagtt gctcctctca      60
gagcagaatc gggtattcaa caccctcata tcaactacta cgttgtgtat aacggtccac     120
atgccggtat atacgatgac tggggttgta caaaggcggc aacaaacggc gttcccggag     180
ttgcacacaa gaaatttgcc actattacag aggcaagagc agcagctgac gcgtacacaa     240
caagtcagca aacagacagg ttgaacttca tccccaaagg agaagctcaa ctcaagccca     300
agagctttgc taaggcccta acaagcccac caaagcaaaa agcccactgg ctcacgctag     360
gaaccaaaag gcccagcagt gatccagccc caaagagat ctcctttgcc ccggagatta     420
caatggacga tttcctctat ctttacgatc taggaaggaa gttcgaaggt gaaggtgacg     480
acactatgtt caccactgat aatgagaagg ttagcctctt caatttcaga agaatgctg     540 acccacagat ggttagagag gcctacgcag caggtctcat caagacgatc tacccgagta     600
acaatctcca ggagatcaaa taccttccca agaaggttaa agatgcagtc aaaagattca     660
ggactaattg catcaagaac acagagaaag acatatttct caagatcaga agtactattc     720
cagtatggac gattcaaggc ttgcttcata aaccaaggca agtaatagag attggagtct     780
ctaaaaaggt agttcctact gaatctaagg ccatgcatgg agtctaagat tcaaatcgag     840
gatctaacag aactcgccgt gaagactggc gaacagttca tacagagtct tttacgactc     900
aatgacaaga agaaaatctt cgtcaacatg gtggagcacg acactctggt ctactccaaa     960
aatgtcaaag atacagtctc agaagaccaa agggctattg agacttttca acaaaggata    1020
atttcgggaa acctcctcgg attccattgc ccagctatct gtcacttcat cgaaaggaca    1080
gtagaaaagg aaggtggctc ctacaaatgc catcattgcg ataaaggaaa ggctatcatt    1140
caagatctct ctgccgacag tggtcccaaa gatggacccc cacccacgag gagcatcgtg    1200
gaaaaagaag acgttccaac cacgtcttca aagcaagtgg attgatgtga catctccact    1260
gacgtaaggg atgacgcaca atcccactat ccttcgcaag acccttcctc tatataagga    1320
agttcatttc atttgga                                                   1337
```

<210> SEQ ID NO 5
<211> LENGTH: 752
<212> TYPE: DNA
<213> ORGANISM: Flaveria trinervia

<400> SEQUENCE: 5

```
ataattattt tctttttttcc ttttagtata aaatagttaa gtgatgttaa ttagtatgat     60
tataataata tagttgttat aattgtgaaa aaataaattta taaatatatt gtttacataa    120
```

| | |
|---|---|
| acaacatagt aatgtaaaaa aatatgacaa gtgatgtgta agacgaagaa gataaaagtt | 180 |
| gagagtaagt atattatttt taatgaattt gatcgaacat gtaagatgat atactagcat | 240 |
| taatatttgt tttaatcata atagtaattc tagctggttt gatgaattaa atatcaatga | 300 |
| taaaatacta tagtaaaaat aagaataaat aaattaaaat aatatttttt tatgattaat | 360 |
| agtttattat ataattaaat atctatacca ttactaaata ttttagttta aaagttaata | 420 |
| aatatttgt tagaaattcc aatctgcttg taatttatca ataaacaaaa tattaaataa | 480 |
| caagctaaag taacaaataa tatcaaacta atagaaacag taatctaatg taacaaaaca | 540 |
| taatctaatg ctaatataac aaagcgcaag atctatcatt ttatatagta ttattttcaa | 600 |
| tcaacattct tattaatttc taaataatac ttgtagtttt attaacttct aaatggattg | 660 |
| actattaatt aaatgaatta gtcgaacatg aataaacaag gtaacatgat agatcatgtc | 720 |
| attgtgttat cattgatctt acatttggat tg | 752 |

<210> SEQ ID NO 6
<211> LENGTH: 707
<212> TYPE: DNA
<213> ORGANISM: Agrobacterium tumefaciens

<400> SEQUENCE: 6

| | |
|---|---|
| ctgctttaat gagatatgcg agacgcctat gatcgcatga tatttgcttt caattctgtt | 60 |
| gtgcacgttg taaaaaacct gagcatgtgt agctcagatc cttaccgccg gtttcggttc | 120 |
| attctaatga atatatcacc cgttactatc gtatttttat gaataatatt ctccgttcaa | 180 |
| tttactgatt gtaccctact acttatatgt acaatattaa aatgaaaaca atatattgtg | 240 |
| ctgaataggt ttatagcgac atctatgata gagcgccaca ataacaaaca attgcgtttt | 300 |
| attattacaa atccaatttt aaaaaagcg gcagaaccgg tcaaacctaa aagactgatt | 360 |
| acataaatct tattcaaatt tcaaaaggcc ccaggggcta gtatctacga cacaccgagc | 420 |
| ggcgaactaa taacgttcac tgaagggaac tccggttccc cgccggcgcg catgggtgag | 480 |
| attccttgaa gttgagtatt ggccgtccgc tctaccgaaa gttacgggca ccattcaacc | 540 |
| cggtccagca cggcggccgg gtaaccgact tgctgccccg agaattatgc agcattttt | 600 |
| tggtgtatgt gggccccaaa tgaagtgcag gtcaaacctt gacagtgacg acaaatcgtt | 660 |
| gggcgggtcc agggcgaatt ttgcgacaac atgtcgaggc tcagcag | 707 |

<210> SEQ ID NO 7
<211> LENGTH: 1402
<212> TYPE: DNA
<213> ORGANISM: Arabidopsis thaliana

<400> SEQUENCE: 7

| | |
|---|---|
| aaaatttaga acgaacttaa ttatgatctc aaatacattg atacatatct catctagatc | 60 |
| taggttatca ttatgtaaga aagttttgac gaatatggca cgacaaaatg gctagactcg | 120 |
| atgtaattgg tatctcaact caacattata cttataccaa acattagtta gacaaaattt | 180 |
| aaacaactat tttttatgta tgcaagagtc agcatatgta taattgattc agaatcgttt | 240 |
| tgacgagttc ggatgtagta gtagccatta tttaatgtac atactaatcg tgaatagtga | 300 |
| atatgatgaa acattgtatc ttattgtata aatatccata aacacatcat gaaagacact | 360 |
| ttctttcacg gtctgaatta attatgatac aattctaata gaaaacgaat taaattacgt | 420 |
| tgaattgtat gaaatctaat tgaacaagcc aaccacgacg acgactaacg ttgcctggat | 480 |

| | |
|---|---|
| tgactcggtt taagttaacc actaaaaaaa cggagctgtc atgtaacacg cggatcgagc | 540 |
| aggtcacagt catgaagcca tcaaagcaaa agaactaatc caagggctga gatgattaat | 600 |
| tagtttaaaa attagttaac acgagggaaa aggctgtctg acagccaggt cacgttatct | 660 |
| ttacctgtgg tcgaaatgat tcgtgtctgt cgatttttaat tatttttttg aaaggccgaa | 720 |
| aataaagttg taagagataa acccgcctat ataaattcat atattttcct ctccgctttg | 780 |
| aattgtctcg ttgtcctcct cactttcatc agccgttttg aatctccggc gacttgacag | 840 |
| agaagaacaa ggaagaagac taagagagaa agtaagagat aatccaggag attcattctc | 900 |
| cgttttgaat cttcctcaat ctcatcttct tccgctcttt cttccaagg taataggaac | 960 |
| tttctggatc tactttattt gctggatctc gatcttgttt tctcaatttc cttgagatct | 1020 |
| ggaattcgtt taatttggat ctgtgaacct ccactaaatc ttttggtttt actagaatcg | 1080 |
| atctaagttg accgatcagt tagctcgatt atagctacca gaatttggct tgaccttgat | 1140 |
| ggagagatcc atgttcatgt tacctgggaa atgatttgta tatgtgaatt gaaatctgaa | 1200 |
| ctgttgaagt tagattgaat ctgaacactg tcaatgttag attgaatctg aacactgtttt | 1260 |
| aaggttagat gaagtttgtg tatagattct tcgaaacttt aggatttgta gtgtcgtacg | 1320 |
| ttgaacagaa agctatttct gattcaatca gggtttattt gactgtattg aactcttttt | 1380 |
| gtgtgtttgc agctcataaa aa | 1402 |

<210> SEQ ID NO 8
<211> LENGTH: 1812
<212> TYPE: DNA
<213> ORGANISM: Escherichia coli

<400> SEQUENCE: 8

| | |
|---|---|
| atgttacgtc ctgtagaaac cccaacccgt gaaatcaaaa aactcgacgg cctgtgggca | 60 |
| ttcagtctgg atcgcgaaaa ctgtggaatt gatcagcgtt ggtgggaaag cgcgttacaa | 120 |
| gaaagccggg caattgctgt gccaggcagt tttaacgatc agttcgccga tgcagatatt | 180 |
| cgtaattatg cgggcaacgt ctggtatcag cgcgaagtct ttataccgaa aggttgggca | 240 |
| ggccagcgta tcgtgctgcg tttcgatgcg gtcactcatt acggcaaagt gtgggtcaat | 300 |
| aatcaggaag tgatggagca tcagggcggc tatacgccat tgaagccga tgtcacgccg | 360 |
| tatgttattg ccgggaaaag tgtacgtatc accgtttgtg tgaacaacga actgaactgg | 420 |
| cagactatcc cgccgggaat ggtgattacc gacgaaaacg gcaagaaaaa gcagtcttac | 480 |
| ttccatgatt tctttaacta tgccggaatc catcgcagcg taatgctcta caccacgccg | 540 |
| aacacctggg tggacgatat caccgtggtg acgcatgtcg cgcaagactg taaccacgcg | 600 |
| tctgttgact ggcaggtggt ggccaatggt gatgtcagcg ttgaactgcg tgatgcggat | 660 |
| caacaggtgg ttgcaactgg acaaggcact agcgggactt tgcaagtggt gaatccgcac | 720 |
| ctctggcaac cgggtgaagg ttatctctat gaactgtgcg tcacagccaa agcccagaca | 780 |
| gagtgtgata tctacccgct tcgcgtcggc atccggtcag tggcagtgaa gggcgaacag | 840 |
| ttcctgatta accacaaacc gttctactttt actggctttg gtcgtcatga agatgcggac | 900 |
| ttgcgtggca aaggattcga taacgtgctg atggtgcacg accacgcatt aatggactgg | 960 |
| attgggcca actcctaccg tacctcgcat taccctttacg ctgaagagat gctcgactgg | 1020 |
| gcagatgaac atggcatcgt ggtgattgat gaaactgctg ctgtcggctt taacctctct | 1080 |
| ttaggcattg gtttcgaagc gggcaacaag ccgaaagaac tgtacagcga agaggcagtc | 1140 |
| aacgggaaa ctcagcaagc gcacttacag gcgattaaag agctgatagc gcgtgacaaa | 1200 |

| | |
|---|---|
| aaccacccaa gcgtggtgat gtggagtatt gccaacgaac cggatacccg tccgcaaggt | 1260 |
| gcacgggaat atttcgcgcc actggcggaa gcaacgcgta aactcgaccc gacgcgtccg | 1320 |
| atcacctgcg tcaatgtaat gttctgcgac gctcacaccg ataccatcag cgatctcttt | 1380 |
| gatgtgctgt gcctgaaccg ttattacgga tggtatgtcc aaagcggcga tttggaaacg | 1440 |
| gcagagaagg tactggaaaa agaacttctg gcctggcagg agaaactgca tcagccgatt | 1500 |
| atcatcaccg aatacggcgt ggatacgtta gccgggctgc actcaatgta caccgacatg | 1560 |
| tggagtgaag agtatcagtg tgcatggctg gatatgtatc accgcgtctt tgatcgcgtc | 1620 |
| agcgccgtcg tcggtgaaca ggtatggaat ttcgccgatt ttgcgacctc gcaaggcata | 1680 |
| ttgcgcgttg gcggtaacaa gaaagggatc ttcactcgcg accgcaaacc gaagtcggcg | 1740 |
| gcttttctgc tgcaaaaacg ctggactggc atgaacttcg gtgaaaaacc gcagcaggga | 1800 |
| ggcaaacaat ga | 1812 |

<210> SEQ ID NO 9
<211> LENGTH: 262
<212> TYPE: DNA
<213> ORGANISM: Agrobacterium tumefaciens

<400> SEQUENCE: 9

| | |
|---|---|
| gatcgttcaa acatttggca ataaagtttc ttaagattga atcctgttgc cggtcttgcg | 60 |
| atgattatca tataatttct gttgaattac gttaagcatg taataattaa catgtaatgc | 120 |
| atgacgttat ttatgagatg ggttttttatg attagagtcc cgcaattata catttaatac | 180 |
| gcgatagaaa acaaaatata gcgcgcaaac taggataaat tatcgcgcgc ggtgtcatct | 240 |
| atgttactag atcgggaatt cg | 262 |

<210> SEQ ID NO 10
<211> LENGTH: 589
<212> TYPE: DNA
<213> ORGANISM: Escherichia coli

<400> SEQUENCE: 10

| | |
|---|---|
| ttgagatcct ttttttctgc gcgtaatctg ctgcttgcaa acaaaaaaac caccgctacc | 60 |
| agcggtggtt tgtttgccgg atcaagagct accaactctt tttccgaagg taactggctt | 120 |
| cagcagagcg cagataccaa atactgtcct tctagtgtag ccgtagttag gccaccactt | 180 |
| caagaactct gtagcaccgc ctacatacct cgctctgcta atcctgttac cagtggctgc | 240 |
| tgccagtggc gataagtcgt gtcttaccgg gttggactca agacgatagt taccggataa | 300 |
| ggcgcagcgg tcgggctgaa cggggggttc gtgcacacag cccagcttgg agcgaacgac | 360 |
| ctacaccgaa ctgagatacc tacagcgtga gctatgagaa agcgccacgc ttcccgaagg | 420 |
| gagaaaggcg gacaggtatc cggtaagcgg cagggtcgga acaggagagc gcacgaggga | 480 |
| gcttccaggg ggaaacgcct ggtatcttta tagtcctgtc gggtttcgcc acctctgact | 540 |
| tgagcgtcga ttttttgtgat gctcgtcagg ggggcggagc ctatggaaa | 589 |

<210> SEQ ID NO 11
<211> LENGTH: 861
<212> TYPE: DNA
<213> ORGANISM: Escherichia coli

<400> SEQUENCE: 11

| | |
|---|---|
| atgagtattc aacatttccg tgtcgccctt attccctttt ttgcggcatt ttgccttcct | 60 |

-continued

```
gtttttgctc acccagaaac gctggtgaaa gtaaaagatg ctgaagatca gttgggtgca    120
cgagtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga caccacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatggatgaa cgaaatagac agatcgctga gataggtgcc    840
tcactgatta agcattggta a                                              861
```

<210> SEQ ID NO 12
<211> LENGTH: 461
<212> TYPE: DNA
<213> ORGANISM: Ricinus communis

<400> SEQUENCE: 12

```
acatgaaata ccagtgttgc caaacagagt tggtttgcct ataaaccaac ggtttatttt     60
agttgaactc tcaaatcatg cagagctttc tgttacatta gcgctggatg tcaccaatgc    120
atatgtggtc ggctaccgag ctggaaatag cgcatatttc tttcatcctg acaatcagga    180
agatgcagaa gcaatcactc atcttttcac tgatgttcaa aatcgatata cattcgcctt    240
tggtggtaat tatgatagac ttgaacaact tgccggtagt ctgagagaaa atatcgagtt    300
gggaaatggt ccactagagg aggctatctc agcgctttat tattacagta ctggtggcac    360
tcagcttcca actctggctc gttcctttat agtttgcatc caaatgattt cagaagcagc    420
aagattccaa tatattgagg gagaaatgcg cacgagaatt a                        461
```

<210> SEQ ID NO 13
<211> LENGTH: 461
<212> TYPE: DNA
<213> ORGANISM: Ricinus communis

<400> SEQUENCE: 13

```
taattctcgt gcgcatttct ccctcaatat attggaatct tgctgcttct gaaatcattt     60
ggatgcaaac tataaaggaa cgagccagag ttggaagctg agtgccacca gtactgtaat    120
aataaagcgc tgagatagcc tcctctagtg gaccatttcc caactcgata ttttctctca    180
gactaccggc aagttgttca agtctatcat aattaccacc aaaggcgaat gtatatcgat    240
tttgaacatc agtgaaaaga tgagtgattg cttctgcatc ttcctgattg tcaggatgaa    300
agaaatatgc gctatttcca gctcggtagc cgaccacata tgcattggtg acatccagcg    360
ctaatgtaac agaaagctct gcatgatttg agagttcaac taaaataaac cgttggttta    420
taggcaaacc aactctgttt ggcaacactg gtatttcatg t                        461
```

<210> SEQ ID NO 14
<211> LENGTH: 16178

```
<212> TYPE: DNA
<213> ORGANISM: Artificial Sequence
<220> FEATURE:
<223> OTHER INFORMATION: Synthetic sequence, vector

<400> SEQUENCE: 14
cacctaaatt gtaagcgtta atattttgtt aaaattcgcg ttaaattttt gttaaatcag      60
ctcattttt  aaccaatagg ccgaaatcgg caaatccct  tataaatcaa aagaatagac     120
cgagataggg ttgagtgttg ttccagtttg aacaagagt  ccactattaa agaacgtgga    180
ctccaacgtc aaagggcgaa aaaccgtcta tcagggcgat ggcccactac gtgaaccatc    240
accctaatca gtttttttgg ggtcgaggtg ccgtaaagca ctaaatcgga accctaaagg    300
gagcccccga tttagagctt gacggggaaa gccggcgaac gtggcgagaa aggaagggaa    360
gaaagcgaaa ggagcgggcg ctagggcgct ggcaagtgta gcggtcacgc tgcgcgtaac    420
caccacaccc gccgcgctta atgcgccgct acagggcgcg tcccattcgc cattcaggct    480
gcgcaactgt tgggaagggc gatcggtgcg ggcctcttcg ctattacgcc agctggcgaa    540
agggggatgt gctgcaaggc gattaagttg ggtaacgcca gggttttccc agtcacgacg    600
ttgtaaaacg acggccagtg aattgtaata cgactcacta tagggcgaat tggagctcca    660
ccgcggtggc ggccgcagat ttaggtgaca ctatagaata tgcatcacta gtaagctagc    720
ttgcatgcct gcaggtcctg ctgagcctcg acatgttgtc gcaaaattcg ccctggaccc    780
gcccaacgat ttgtcgtcac tgtcaaggtt tgacctgcac ttcatttggg gcccacatac    840
accaaaaaaa tgctgcataa ttctcggggc agcaagtcgg ttaccggcc  gccgtgctgg    900
accgggttga atggtgcccg taactttcgg tagagcggac ggccaatact caacttcaag    960
gaatctcacc catgcgcgcc ggcggggaac cggagttccc ttcagtgaac gttattagtt   1020
cgccgctcgg tgtgtcgtag atactagccc ctggggcctt ttgaaatttg aataagattt   1080
atgtaatcag tcttttaggt ttgaccggtt ctgccgcttt ttttaaaatt ggatttgtaa   1140
taataaaacg caattgtttg ttattgtggc gctctatcat agatgtcgct ataaacctat   1200
tcagcacaat atattgtttt cattttaata ttgtacatat aagtagtagg gtacaatcag   1260
taaattgaac ggagaatatt attcataaaa atacgatagt aacgggtgat atattcatta   1320
gaatgaaccg aaaccggcgg taaggatctg agctacacat gctcaggttt tttacaacgt   1380
gcacaacaga attgaaagca aatatcatgc gatcataggc gtctcgcata tctcattaaa   1440
gcaggactct agactcgaga catgaaatac cagtgttgcc aaacagagtt ggtttgccta   1500
taaaccaacg gttatttta  gttgaactct caaatcatgc agagctttct gttacattag   1560
cgctggatgt caccaatgca tatgtggtcg gctaccgagc tggaaatagc gcatatttct   1620
ttcatcctga caatcaggaa gatgcagaag caatcactca tcttttcact gatgttcaaa   1680
atcgatatac attcgccttt ggtggtaatt atgatagact tgaacaactt gccggtagtc   1740
tgagagaaaa tatcgagttg ggaaatggtc cactagagga ggctatctca gcgctttatt   1800
attacagtac tggtggcact cagcttccaa ctctggctcg ttcctttata gtttgcatcc   1860
aaatgatttc agaagcagca agattccaat atattgaggg agaaatgcgc acgagaatta   1920
ggtaccaagc ttatcgattt cgaacccaat ttcccaactg taatcaatcc aaatgtaaga   1980
tcaatgataa cacaatgaca tgatctatca tgttaccttg tttattcatg ttcgactaat   2040
tcatttaatt aatagtcaat ccatttagaa gttaataaaa ctacaagtat tatttagaaa   2100
ttaataagaa tgttgattga aaataatact atataaaatg atagatcttg cgctttgtta   2160
```

```
tattagcatt agattatgtt tgttacatt agattactgt ttctattagt ttgatattat    2220
ttgttacttt agcttgttat ttaatatttt gtttattgat aaattacaag cagattggaa    2280
tttctaacaa aatatttatt aacttttaaa ctaaaatatt tagtaatggt atagatattt    2340
aattatataa taaactatta atcataaaaa aatattattt taatttatttt attcttattt    2400
ttactatagt attttatcat tgatatttaa ttcatcaaac cagctagaat tactattatg    2460
attaaaacaa atattaatgc tagtatatca tcttacatgt tcgatcaaat tcattaaaaa    2520
taatatactt actctcaact tttatcttct tcgtcttaca catcacttgt catatttttt    2580
tacattacta tgttgtttat gtaaacaata tattttaaaa ttatttttc acaattataa    2640
caactatatt attataatca tactaattaa catcacttaa ctattttata ctaaaaggaa    2700
aaaagaaaat aattatttcc ttaccaattg gggtacctaa ttctcgtgcg catttctccc    2760
tcaatatatt ggaatcttgc tgcttctgaa atcatttgga tgcaaactat aaaggaacga    2820
gccagagttg gaagctgagt gccaccagta ctgtaataat aaagcgctga gatagcctcc    2880
tctagtggac catttcccaa ctcgatattt tctctcagac taccggcaag ttgttcaagt    2940
ctatcataat taccaccaaa ggcgaatgta tatcgattt gaacatcagt gaaaagatga    3000
gtgattgctt ctgcatcttc ctgattgtca ggatgaaaga aatatgcgct atttccagct    3060
cggtagccga ccacatatgc attggtgaca tccagcgcta atgtaacaga aagctctgca    3120
tgatttgaga gttcaactaa aataaaccgt tggtttatag gcaaaccaac tctgtttggc    3180
aacactggta tttcatgtct cgagcgtgtc ctctccaaat gaaatgaact tccttatata    3240
gaggaagggt cttgcgaagg atagtgggat tgtgcgtcat cccttacgtc agtggagatg    3300
tcacatcaat ccacttgctt tgaagacgtg gttggaacgt cttcttttc cacgatgctc    3360
ctcgtgggtg ggggtccatc tttgggacca ctgtcggcag agagatcttg aatgatagcc    3420
tttcctttat cgcaatgatg gcatttgtag gagccacctt ccttttctac tgtcctttcg    3480
atgaagtgac agatagctgg gcaatggaat ccgaggaggt ttcccgaaat tatcctttgt    3540
tgaaaagtct caatagccct ttggtcttct gagactgtat ctttgacatt tttggagtag    3600
accagagtgt cgtgctccac catgttgacg aagattttct tcttgtcatt gagtcgtaaa    3660
agactctgta tgaactgttc gccagtcttc acggcgagtt ctgttagatc ctcgatttga    3720
atcttagact ccatgcatgg ccttagattc agtaggaact acctttttag agactccaat    3780
ctctattact tgccttggtt tatgaagcaa gccttgaatc gtccatactg gaatagtact    3840
tctgatcttg agaaatatgt cttttctctgt gttcttgatg caattagtcc tgaatctttt    3900
gactgcatct ttaaccttct tgggaaggta tttgatctcc tggagattgt tactcgggta    3960
gatcgtcttg atgagacctg ctgcgtaggc ctctctaacc atctgtgggt cagcattctt    4020
tctgaaattg aagaggctaa ccttctcatt atcagtggtg aacatagtgt cgtcaccttc    4080
accttcgaac ttccttccta gatcgtaaag atagaggaaa tcgtccattg taatctccgg    4140
ggcaaaggag atctcttttg gggctggatc actgctgggc ttttggttc ctagcgtgag    4200
ccagtgggct ttttgctttg gtgggcttgt tagggcctta gcaaagctct tgggcttgag    4260
ttgagcttct ccttgggga tgaagttcaa cctgtctgtt tgctgacttg ttgtgtacgc    4320
gtcagctgct gctcttgcct ctgtaatagt ggcaaatttc ttgtgtgcaa ctccgggaac    4380
gccgttttgtt gccgccttg tacaacccca gtcatcgtat ataccggcat gtggaccgtt    4440
atacacaacg tagtagttga tatgagggtg ttgaataccc gattctgctc tgagaggagc    4500
aactgtgctg ttaagctcag atttttgtgg gattggaatt aattcgtcga gcggccgctc    4560
```

```
tagattatgt atttccaact ttcattaaca atataatcgc atataaatga aaaatcgttt    4620
ccaggataat attttgatga aatctcatat tattgttcgt actcggattg atgttgaagg    4680
cttgaagcgc ttcaaattat agaccagatt atttaagttt ttcttttgtt tactccatat    4740
caatttgatc cattatacta cctaagaaaa tttaggtaac atagaattat ttattgttat    4800
agtaaaaaaa aggaaaacca caaaataat ctacttttac gtatatacta ttttcatgac     4860
ataagtaatt aagttgtaca actttttttt aatgaaaaga gagagtaaat ttatcatgtt    4920
catgtgtagt tacctcgtga ataaccgacg ttatataga cgcctaacat gaattgttca    4980
gttgaagaca gttcaaaaca tgtgtttcac tctaaaatcc tcaacaaaaa aaagtgtta    5040 aaatttgtaa acctctttca agcaaaaaaa gaaaaagtgt tagaatccca agattctttc    5100
ataatccgga atcttggctg aaaacgtata aagagattg acgtagtaac aaggagtctt    5160
ggtatgcttc catgcttttt atcctttttt gtcatggaac catgatttgg ttaccattta    5220
ttatgtaacc gaaattttca ttgtaataat gaatatttaa attttagca aaaaaaaaca    5280 aaaaaaaaca aggagtcttg tcttcgttct caaatttcag agctcttgca cttttcaaga    5340 gtttacttt tgatgagtgag acatttgtct ttttagtgtt tattttctaa acttaaaata    5400
gtagcatcaa catcactcaa ttataattct taagatgttg tagaaaaata ttttatagat    5460
ggaaagtaat cgatattaag acaaataaga aaccaaaccg gactttgtgt tcagaccgaa    5520
tcaaatctga attggagaaa ttatggtgga ggcgaaagtc aacggaacta agtataaaa     5580 ccaaatgtca aaataaaac ccaattttca tccttaaacg aacctgctga aaccctaatt     5640
tcgattacca attccgatct aaaagaagt catggaagcc attgattccg caatcgatcc     5700
tctcagagat ttcgctaaga gcagtgttcg tctcgtccag cgctgtcaca aacccgatcg    5760
caagggtaac gccttttctc aaaaaaatct catttccgat ttttgatctg tagattaggg    5820
ttttctgaaa ttttgatatc atttgtaatt gaattggtta tcagaattca cgaaagtagc    5880
tgtgcgtacg gcgattggat ttgtggtgat gggattcgtt ggattcttcg tgaagctcgt    5940
tttcatccca atcaacaaca tcatcgttgg atcttcttag tgtagtactt tctttacgag    6000
gtaattgatc tcgcattata tatctacatt ttggttatgt tacttgacat atagtcattg    6060
attcaatagt tctgttaatt cctttaaaga tcattttgac tagaccacat tcttggttca    6120
ttcctcaata atttgtaatc atattggtgg atatagaagt agattggtta tagatcagat    6180
agtggaagac tttaggatga atttcagcta gttttttttt ttggcttatt gtctcaaaag    6240
attagtgctt tgctgtctcc attgcttctg ctatcgacac gcttctgtct ccttgtatct    6300
ttattatatc tattcgtccc atgagttttg tttgttctgt attcgttcgc tctggtgtca    6360
tggatggagt ctctgttcca tgtttctgta atgcatgttg ggttgtttca tgcaagaaat    6420
gctgagataa acactcattt gtgaaagttt ctaaactctg aatcgcgcta caggcaatgc    6480
tccgaggagt aggaggagaa gaacgaacca aacgacatta tcagcccttt gaggaagctc    6540
ttagttttgt tattgttttt gtagccaaat tctccattct tattccattt tcacttatct    6600
cttgttcctt atagacctta taagtttttt attcatgtat acaaattata ttgtcatcaa    6660
gaagtatctt taaaatctaa atctcaaatc accaggacta tgttttgtc caattcgtgg     6720 aaccaacttg cagcttgtat ccattctctt aaccaataaa aaagaaaga aagatcaatt     6780 tgataaattt ctcagccaca aattctacat ttaggtttta gcatatcgaa ggctcaatca    6840
caaatacaat agatagacta gagattccag cgtcacgtga gttttatcta taaataaagg    6900
```

```
accaaaaatc aaatcccgag ggcattttcg taatccaaca taaaacccft aaacttcaag    6960
tctcattttt aaacaaatca tgttcacaag tctcttcttc ttctctgttt ctctatctct    7020
tgctcatctt tctcctgaac catggcggcg gcaacaacaa caacaacaac atcttcttcg    7080
atctccttct ccaccaaacc atctccttcc tcctccaaat caccattacc aatctccaga    7140
ttctccctcc cattctccct aaaccccaac aaatcatcct cctcctcccg ccgccgcggt    7200
atcaaatcca gctctccctc ctccatctcc gccgtgctca acacaaccac caatgtcaca    7260
accactccct ctccaaccaa acctaccaaa cccgaaacat tcatctcccg attcgctcca    7320
gatcaacccc gcaaaggcgc tgatatcctc gtcgaagctt tagaacgtca aggcgtagaa    7380
accgtattcg cttaccctgg aggtgcatca atggagattc accaagcctt aacccgctct    7440
tcctcaatcc gtaacgtcct tcctcgtcac gaacaaggag gtgtattcgc agcagaagga    7500
tacgctcgat cctcaggtaa accaggtatc tgtatagcca cttcaggtcc cggagctaca    7560
aatctcgtta gcggattagc cgatgcgttg ttagatagtg ttcctcttgt agcaatcaca    7620
ggacaagtcc ctcgtcgtat gattggtaca gatgcgtttc aagagactcc gattgttgag    7680
gtaacgcgtt cgattacgaa gcataactat cttgtgatgg atgttgaaga tatccctagg    7740
attattgagg aagctttctt tttagctact tctggtagac ctggacctgt tttggttgat    7800
gttcctaaag atattcaaca acagcttgcg attcctaatt gggaacaggc tatgagatta    7860
cctggttata tgtctaggat gcctaaacct ccggaagatt tcatttgga gcagattgtt     7920
aggttgattt ctgagtctaa gaagcctgtg ttgtatgttg gtggtggttg tttgaattct    7980
agcgatgaat tgggtaggtt tgttgagctt acggggatcc ctgttgcgag tacgttgatg    8040
gggctgggat cttatccttg tgatgatgag ttgtcgttac atatgcttgg aatgcatggg    8100
actgtgtatg caaattacgc tgtggagcat agtgatttgt tgttggcgtt tggggtaagg    8160
tttgatgatc gtgtcacggg taagcttgag gcttttgcta gtagggctaa gattgttcat    8220
attgatattg actcggctga gattgggaag aataagactc tcatgtgtc tgtgtgtggt     8280
gatgttaagc tggctttgca agggatgaat aaggttcttg agaaccgagc ggaggagctt    8340
aagcttgatt ttggagtttg gaggaatgag ttgaacgtac agaaacagaa gtttccgttg    8400
agctttaaga cgtttgggga agctattcct ccacagtatg cgattaaggt ccttgatgag    8460
ttgactgatg gaaaagccat aataagtact ggtgtcgggc aacatcaaat gtgggcggcg    8520
cagttctaca attacaagaa accaaggcag tggctatcat caggaggcct tggagctatg    8580
ggatttggac ttcctgctgc gattggagcg tctgttgcta accctgatgc gatagttgtg    8640
gatattgacg gagatggaag ctttataatg aatgtgcaag agctagccac tattcgtgta    8700
gagaatcttc cagtgaaggt acttttatta aacaaccagc atcttggcat ggttatgcaa    8760
tgggaagatc ggttctacaa agctaaccga gctcacacat ttctcgggga tccggctcag    8820
gaggacgaga tattcccgaa catgttgctg tttgcagcag cttgcgggat tccagcggcg    8880
agggtgacaa agaaagcaga tctccgagaa gctattcaga caatgctgga tacaccagga    8940
ccttacctgt tggatgtgat tgttccgcac caagaacatg tgttgccgat gatcccgagt    9000
ggtggcactt tcaacgatgt cataacggaa ggagatggcc ggattaaata ctgagagatg    9060
aaaccggtga ttatcagaac ctttttatgg cttttgtatgc atatggtaaa aaaacttagt    9120
ttgcaatttc ctgttttgttt tggtaatttg agtttctttt agttgttgat ctgcctgctt    9180
tttggtttac gtcagactac tactgctgtt gttgtttggt ttccttttctt tcatttata    9240
aataaataat ccggttcggt ttactccttg tgactggctc agtttggtta ttgcgaaatg    9300
```

-continued

```
cgaatggtaa attgagtaat tgaaattcgt tattagggtt ctaagctgtt ttaacagtca    9360
ctgggttaat atctctcgaa tcttgcatgg aaaatgctct taccattggt ttttaattga    9420
aatgtgctca tatgggccgt ggtttccaaa ttaaataaaa ctacgatgtc atcgagaagt    9480
aaaatcaact gtgtccacat tatcagtttt gtgtatacga tgaaataggg taattcaaaa    9540
tctagcttga tatgccttt tggttcatttt aaccttctgt aaacattttt tcagattttg    9600
aacaagtaaa tccaaaaaaa aaaaaaaaa aatctcaact caacactaaa ttatttttaat    9660 gtataaaaga tgcttaaaac atttggctta aagaaagaa gctaaaaaca tagagaactc    9720
ttgtaaattg aagtatgaaa atatactgaa ttgggtatta tatgaatttt tctgatttag    9780
gattcacatg atccaaaaag gaaatccaga agcactaatc agacattgga agtaggaata    9840
tttcaaaaag tttttttttt ttaagtaagt gacaaaagct tttaaaaaat agaaaagaaa    9900
ctagtattaa agttgtaaat ttaataaaca aaagaaattt tttatatttt ttcatttctt    9960
tttccagcat gaggttatga tgcaggatg tggatttcat tttttttcctt ttgatagcct   10020 tttaattgat ctattataat tgacgaaaaa atattagtta attatagata tattttaggt   10080
agtattagca atttacactt ccaaaagact atgtaagttg taaatatgat gcgttgatct   10140
cttcatcatt caatggttag tcaaaaaaat aaaagcttaa ctagtaaact aaagtagtca   10200
aaaattgtac tttagtttaa aatattcat gaataatcca aaacgacatt tatgtgaaac   10260
aaaaacaata tctagaacta gtggatcccc cgggctgcag gtcgacaaaa tttagaacga   10320
acttaattat gatctcaaat acattgatac atatctcatc tagatctagg ttatcattat   10380
gtaagaaagt tttgacgaat atggcacgac aaaatggcta gactcgatgt aattggtatc   10440
tcaactcaac attatactta taccaaacat tagttagaca aaatttaaac aactattttt   10500
tatgtatgca agagtcagca tatgtataat tgattcagaa tcgttttgac gagttcggat   10560
gtagtagtag ccattattta atgtacatac taatcgtgaa tagtgaatat gatgaaacat   10620
tgtatcttat tgtataaata tccataaaca catcatgaaa gacactttct ttcacggtct   10680
gaattaatta tgatacaatt ctaatagaaa acgaattaaa ttacgttgaa ttgtatgaaa   10740
tctaattgaa caagccaacc acgacgacga ctaacgttgc ctggattgac tcggtttaag   10800
ttaaccacta aaaaaacgga gctgtcatgt aacacgcgga tcgagcaggt cacagtcatg   10860
aagccatcaa agcaaaagaa ctaatccaag ggctgagatg attaattagt ttaaaaatta   10920
gttaacacga gggaaaaggc tgtctgacag ccaggtcacg ttatctttac ctgtggtcga   10980
aatgattcgt gtctgtcgat tttaattatt tttttgaaag gccgaaaata aagttgtaag   11040
agataaaccc gcctatataa attcatatat tttcctctcc gctttgaatt gtctcgttgt   11100
cctcctcact ttcatcagcc gttttgaatc tccggcgact tgacagagaa gaacaaggaa   11160
gaagactaag agagaaagta agagataatc caggagattc attctccgtt tgaatcttc   11220 ctcaatctca tcttcttccg ctctttcttt ccaaggtaat aggaactttc tggatctact   11280
ttatttgctg gatctcgatc ttgttttctc aatttccttg agatctggaa ttcgtttaat   11340
ttggatctgt gaacctccac taaatctttt ggttttacta gaatcgatct aagttgaccg   11400
atcagttagc tcgattatag ctaccagaat ttggcttgac cttgatgagg agatccatgt   11460
tcatgttacc tgggaaatga tttgtatatg tgaattgaaa tctgaactgt tgaagttaga   11520
ttgaatctga acactgtcaa tgttagattg aatctgaaca ctgtttaagg ttagatgaag   11580
tttgtgtata gattcttcga aactttagga tttgtagtgt cgtacgttga acagaaagct   11640
```

```
atttctgatt caatcagggt ttatttgact gtattgaact cttttttgtgt gtttgcagct    11700 cataaaaaat ggctgaggct gacgatattc aaccaatcgt gtgcgacaat ggtactggaa    11760
tggtaggatc cccgggtggt cagtcccctta tgttacgtcc tgtagaaacc ccaacccgtg   11820
aaatcaaaaa actcgacggc ctgtgggcat tcagtctgga tcgcgaaaac tgtggaattg   11880
atcagcgttg gtgggaaagc gcgttacaag aaagccgggc aattgctgtg ccaggcagtt   11940
ttaacgatca gttcgccgat gcagatattc gtaattatgc gggcaacgtc tggtatcagc   12000
gcgaagtctt tataccgaaa ggttgggcag gccagcgtat cgtgctgcgt ttcgatgcgg   12060
tcactcatta cggcaaagtg tgggtcaata atcaggaagt gatggagcat cagggcggct   12120
atacgccatt tgaagccgat gtcacgccgt atgttattgc cgggaaaagt gtacgtatca   12180
ccgtttgtgt gaacaacgaa ctgaactggc agactatccc gccgggaatg gtgattaccg   12240
acgaaaacgg caagaaaaag cagtcttact tccatgattt ctttaactat gccggaatcc   12300
atcgcagcgt aatgctctac accacgccga acacctgggt ggacgatatc accgtggtga   12360
cgcatgtcgc gcaagactgt aaccacgcgt ctgttgactg gcaggtggtg gccaatggtg   12420
atgtcagcgt tgaactgcgt gatgcggatc aacaggtggt tgcaactgga caaggcacta   12480
gcgggacttt gcaagtggtg aatccgcacc tctggcaacc gggtgaaggt tatctctatg   12540
aactgtgcgt cacagccaaa agccagacag agtgtgatat ctacccgctt cgcgtcggca   12600
tccggtcagt ggcagtgaag ggcgaacagt tcctgattaa ccacaaaccg ttctacttta   12660
ctggctttgg tcgtcatgaa gatgcggact gcgtggcaa aggattcgat aacgtgctga   12720
tggtgcacga ccacgcatta atggactgga ttggggccaa ctcctaccgt acctcgcatt   12780
acccttacgc tgaagagatg ctcgactggg cagatgaaca tggcatcgtg gtgattgatg   12840
aaactgctgc tgtcggcttt aacctctctt taggcattgg tttcgaagcg ggcaacaagc   12900
cgaaagaact gtacagcgaa gaggcagtca acggggaaac tcagcaagcg cacttacagg   12960
cgattaaaga gctgatagcg cgtgacaaaa accacccaag cgtggtgatg tggagtattg   13020
ccaacgaacc ggatacccgt ccgcaaggtg cacgggaata tttcgcgcca ctggcggaag   13080
caacgcgtaa actcgacccg acgcgtccga tcacctgcgt caatgtaatg ttctgcgacg   13140
ctcacaccga taccatcagc gatctctttg atgtgctgtg cctgaaccgt tattacggat   13200
ggtatgtcca aagcggcgat ttggaaacgg cagagaaggt actggaaaaa gaacttctgg   13260
cctggcagga gaaactgcat cagccgatta tcatcaccga atacggcgtg gatacgttag   13320
ccgggctgca ctcaatgtac accgacatgt ggagtgaaga gtatcagtgt gcatggctgg   13380
atatgtatca ccgcgtcttt gatcgcgtca gcgccgtcgt cggtgaacag gtatggaatt   13440
tcgccgattt tgcgacctcg caaggcatat tgcgcgttgg cggtaacaag aaagggatct   13500
tcactcgcga ccgcaaaccg aagtcggcgg ctttctgct gcaaaaacgc tggactggca   13560
tgaacttcgg tgaaaaaccg cagcaggag gcaaacaatg aatcaacaac tctcctggcg   13620
caccatcgtc ggctacagcc tcgggaattg ctaccgagct cgaatttccc cgatcgttca   13680
aacatttggc aataaagttt cttaagattg aatcctgttg ccggtcttgc gatgattatc   13740
atataatttc tgttgaatta cgttaagcat gtaataatta acatgtaatg catgacgtta   13800
tttatgagat gggttttttat gattagagtc ccgcaattat acatttaata cgcgatagaa   13860
aacaaaatat agcgcgcaaa ctaggataaa ttatcgcgcg cggtgtcatc tatgttacta   13920
gatcgggaat tcgatatcaa gcttatcgat accgtcgacc tcgagggggg gcccggtacc   13980
cagcttttgt tccctttagt gagggttaat ttcgagcttg gcgtaatcat ggtcatagct   14040
```

-continued

```
gtttcctgtg tgaaattgtt atccgctcac aattccacac aacatacgag ccggaagcat    14100
aaagtgtaaa gcctggggtg cctaatgagt gagctaactc acattaattg cgttgcgctc    14160
actgcccgct ttccagtcgg gaaacctgtc gtgccagctg cattaatgaa tcggccaacg    14220
cgcggggaga ggcggtttgc gtattgggcg ctcttccgct tcctcgctca ctgactcgct    14280
gcgctcggtc gttcggctgc ggcgagcggt atcagctcac tcaaaggcgg taatacggtt    14340
atccacagaa tcaggggata acgcaggaaa gaacatgtga gcaaaaggcc agcaaaaggc    14400
caggaaccgt aaaaaggccg cgttgctggc gtttttccat aggctccgcc ccctgacga    14460
gcatcacaaa aatcgacgct caagtcagag gtggcgaaac ccgacaggac tataaagata    14520
ccaggcgttt ccccctggaa gctccctcgt gcgctctcct gttccgaccc tgccgcttac    14580
cggatacctg tccgcctttc tcccttcggg aagcgtggcg ctttctcata gctcacgctg    14640
taggtatctc agttcggtgt aggtcgttcg ctccaagctg ggctgtgtgc acgaaccccc    14700
cgttcagccc gaccgctgcg ccttatccgg taactatcgt cttgagtcca acccggtaag    14760
acacgactta tcgccactgg cagcagccac tggtaacagg attagcagag cgaggtatgt    14820
aggcggtgct acagagttct tgaagtggtg gcctaactac ggctacacta aggacagt    14880
atttggtatc tgcgctctgc tgaagccagt taccttcgga aaaagagttg gtagctcttg    14940
atccggcaaa caaccaccg ctggtagcgg tggttttttt gtttgcaagc agcagattac    15000
gcgcagaaaa aaggatctc aagaagatcc tttgatcttt tctacggggt ctgacgctca    15060
gtggaacgaa aactcacgtt aagggatttt ggtcatgaga ttatcaaaaa ggatcttcac    15120
ctagatcctt ttaaattaaa aatgaagttt taaatcaatc taaagtatat atgagtaaac    15180
ttggtctgac agttaccaat gcttaatcag tgaggcacct atctcagcga tctgtctatt    15240
tcgttcatcc atagttgcct gactccccgt cgtgtagata actacgatac gggagggctt    15300
accatctggc cccagtgctg caatgatacc gcgagaccca cgctcaccgg ctccagattt    15360
atcagcaata accagccag ccggaagggc cgagcgcaga agtggtcctg caactttatc    15420
cgcctccatc cagtctatta attgttgccg ggaagctaga gtaagtagtt cgccagttaa    15480
tagtttgcgc aacgttgttg ccattgctac aggcatcgtg gtgtcacgct cgtcgtttgg    15540
tatggcttca ttcagctccg gttcccaacg atcaaggcga gttacatgat cccccatgtt    15600
gtgcaaaaaa gcggttagct ccttcggtcc tccgatcgtt gtcagaagta agttggccgc    15660
agtgttatca ctcatggtta tggcagcact gcataattct cttactgtca tgccatccgt    15720
aagatgcttt tctgtgactg gtgagtactc aaccaagtca ttctgagaat agtgtatgcg    15780
gcgaccgagt tgctcttgcc cggcgtcaat acgggataat accgcgccac atagcagaac    15840
tttaaaagtg ctcatcattg gaaaacgttc ttcggggcga aaactctcaa ggatcttacc    15900
gctgttgaga tccagttcga tgtaacccac tcgtgcaccc aactgatctt cagcatcttt    15960
tactttcacc agcgtttctg ggtgagcaaa aacaggaagg caaaatgccg caaaaaaggg    16020
aataagggcg acacggaaat gttgaatact catactcttc cttttcaat attattgaag    16080
catttatcag ggttattgtc tcatgagcgg atacatattt gaatgtattt agaaaaataa    16140
acaaataggg gttccgcgca catttccccg aaaagtgc                          16178
```

<210> SEQ ID NO 15
<211> LENGTH: 20
<212> TYPE: DNA
<213> ORGANISM: Artificial Sequence
<220> FEATURE:

<223> OTHER INFORMATION: Synthetic sequence, primer

<400> SEQUENCE: 15
actagagatt ccagcgtcac                                                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic sequence, primer

<400> SEQUENCE: 16
gtggctatac agatacctgg                                                    20

<210> SEQ ID NO 17
<211> LENGTH: 21
<212> TYPE: DNA
<213> ORGANISM: Artificial Sequence
<220> FEATURE:
<223> OTHER INFORMATION: Synthetic sequence, primer

<400> SEQUENCE: 17
atcacgcagt tcaacgctga c                                                  21

<210> SEQ ID NO 18
<211> LENGTH: 21
<212> TYPE: DNA
<213> ORGANISM: Artificial Sequence
<220> FEATURE:
<223> OTHER INFORMATION: Synthetic sequence, primer

<400> SEQUENCE: 18
ttgggcaggc cagcgtatcg t                                                  21

<210> SEQ ID NO 19
<211> LENGTH: 19
<212> TYPE: DNA
<213> ORGANISM: Artificial Sequence
<220> FEATURE:
<223> OTHER INFORMATION: Synthetic sequence, primer

<400> SEQUENCE: 19
gaacccaatt tcccaactg                                                     19

<210> SEQ ID NO 20
<211> LENGTH: 21
<212> TYPE: DNA
<213> ORGANISM: Artificial Sequence
<220> FEATURE:
<223> OTHER INFORMATION: Synthetic sequence, primer

<400> SEQUENCE: 20
aggtacccca attggtaagg a                                                  21

<210> SEQ ID NO 21
<211> LENGTH: 29
<212> TYPE: DNA
<213> ORGANISM: Artificial Sequence
<220> FEATURE:
<223> OTHER INFORMATION: Synthetic sequence, primer

<400> SEQUENCE: 21
gaagcttggt acctaattct cgtgcgcat                                          29

<210> SEQ ID NO 22
<211> LENGTH: 33
<212> TYPE: DNA
<213> ORGANISM: Artificial Sequence
<220> FEATURE:
<223> OTHER INFORMATION: Synthetic sequence, primer

<400> SEQUENCE: 22
gtctagactc gagacatgaa ataccagtgt tgc                                33

<210> SEQ ID NO 23
<211> LENGTH: 22
<212> TYPE: DNA
<213> ORGANISM: Artificial Sequence
<220> FEATURE:
<223> OTHER INFORMATION: Synthetic sequence, primer

<400> SEQUENCE: 23
gtagccgacc acatatgcat tg                                           22

<210> SEQ ID NO 24
<211> LENGTH: 25
<212> TYPE: DNA
<213> ORGANISM: Artificial Sequence
<220> FEATURE:
<223> OTHER INFORMATION: Synthetic sequence, primer
<220> FEATURE:
<221> NAME/KEY: misc_feature
<222> LOCATION: (22)..(22)
<223> OTHER INFORMATION: n is a, c, g, or t

<400> SEQUENCE: 24
gagacatgaa ataccagtgt tnsgc                                        25

<210> SEQ ID NO 25
<211> LENGTH: 20
<212> TYPE: DNA
<213> ORGANISM: Artificial Sequence
<220> FEATURE:
<223> OTHER INFORMATION: Synthetic sequence, primer

<400> SEQUENCE: 25
tattcttccc aatctcagcc                                              20

<210> SEQ ID NO 26
<211> LENGTH: 24
<212> TYPE: DNA
<213> ORGANISM: Artificial Sequence
<220> FEATURE:
<223> OTHER INFORMATION: Synthetic sequence, primer

<400> SEQUENCE: 26
cctcgggatt tgatttttgg tcct                                         24

<210> SEQ ID NO 27
<211> LENGTH: 396
<212> TYPE: DNA
<213> ORGANISM: Ricinus communis

<400> SEQUENCE: 27
tattcttccc aatctcagcc gagtcaatat caatatgaac aatcttagcc ctactagcaa    60
aagcctcaag cttacccgtg acacgatcat caaaccttac cccaaacgcc aacaacaaat   120
cactatgctc cacaaaaagg ccagcaaaag gccaggaacc gtaaaaaggc cgcgttgctg   180
gcgttttgtc caattcgtgg aaccaacttg cagcttgtat ccattctctt aaccaataaa   240

-continued

```
aaaagaaaga aagatcaatt tgataaattt ctcagccaca aattctacat ttaggtttta    300
gcatatcgaa ggctcaatca caaatacaat agatagacta gagattccag cgtcacgtga    360
gttttatcta taaataaagg accaaaaatc aaatcc                              396
```

METHOD FOR OBTAINING RICIN/RCA-FREE CASTOR-OIL PLANT SEEDS, RICIN/RCA-FREE CASTOR-OIL PLANTS, METHOD FOR IDENTIFYING RICIN/RCA-FREE CASTOR-OIL PLANTS, POLYNUCLEOTIDES, CONSTRUCTS AND USES THEREOF

CROSS REFERENCE TO RELATED APPLICATIONS

This application is a National Stage of International Application No. PCT/BR2019/050480 filed Nov. 6, 2019, claiming priority based on Brazilian Patent Application No. BR102018073082-7 filed Nov. 9, 2018.

FIELD OF INVENTION

This invention relates to the field of plant biotechnology and molecular biology. More specifically, this invention relates to a method for obtaining castor-oil plants deprived of the ricin/RCA protein, through the insertion of gene constructs into plant cells, particularly castor-oil plant ones, with the consequent production of ricin/RCA-free castor-oil plant seeds. Another aspect of the invention refers to obtaining castor-oil plants and parts thereof containing said gene construct. Additionally, this invention provides methods for identifying the plant so transformed, such as identification kit for transformed plants.

DESCRIPTION OF THE STATE OF ART

Castor-oil plant (*Ricinus communis*) is an oil plant from the Euphorbiaceae family, distributed worldwide, but mostly cultivated in tropical and subtropical regions. The most relevant product from this culture is the castor oil, that corresponds to 45-55% of the seed weight. Among the major industrial applications of the castor oil and derivatives thereof, there appear the manufacture of nylon, the production of synthetic resins and fibers, plastics, oil products and artificial leather (Grand View Research, 2016. Castor Oil And Derivatives Market Analysis By Product (Sebacic Acid, Ricinoleic Acid, Undecylenic Acid, Castor Wax, Dehydrated Castor Oil), By Application (Lubricants, Surface Coatings, Biodiesel, Cosmetics & Pharmaceuticals, Plastics& Resins) And Segment Forecasts To 2024.—recovered on Jun. 13, 2018 from https://www.grandviewresearch.com/industry-analysis/castor-oil-derivatives-industry). Castor oil can be also used in the synthesis of renewable monomers and polymers, in the production of soaps, waxes, lubricants, hydraulic fluids (including brake fluids); in the production of coatings and inks, and in the cosmetic, pharmaceutical and food industries (Grand View Research (2016) Castor Oil And Derivatives Market Analysis By Product (Sebacic Acid, Ricinoleic Acid, Undecylenic Acid, Castor Wax, Dehydrated Castor Oil), By Application (Lubricants, Surface Coatings, Biodiesel, Cosmetics & Pharmaceuticals, Plastics& Resins) And Segment Forecasts To 2024—recovered on Jun. 13, 2018 from https://www.grandviewresearch.com/industry-analysis/castor-oil-derivatives-industry). In the cosmetic and perfumery sector, the castor oil is used as emollient, while, in the food industry, it is used as releasing and antiadherent agent for sweeties (FDA, 1984); in the pharmaceutical industry, the castor oil, in addition to its laxative properties, is used as drug delivery vehicle, and as excipient and additive.

Upon extraction of the oil from the castor oil seed, there remains the cake, namely the most important by-product from the culture. The castor oil cake can be used as fertilizer, both for the conventional and the organic agriculture (MELLO, Gabriel Alves Botelho de et al. Organic cultivation of onion under castor cake fertilization and irrigation depths. Acta Sci., Agron., Maringá, v. 40, e34993, 2018. Epub Feb. 5, 2018. http://dx.doi.org/10.4025/actasciagron.v40i1.34993), as it is a significant source of nitrogen, phosphorous, potassium and micronutrients (Lima, R. L. S., Severino, L. S., Sampaio, L. R., Sofiatti, V., Gomes, J. A., Beltrão, N. E. M., 2011. Blends of castor meal and castor husks for optimized use as organic fertilizer. Ind. Crops Prod. 33, 364-368).

The use of castor cake in animal nutrition is prevented by its high toxicity, primarily resulting from the presence of ricin (RCA60), a highly toxic protein, but with low potential for hemagglutination. Moreover, other low toxic components are present, such ricinine, CB-1A complex and RCA120 (Severino L S, 2005. *O que sabemos sobre a torta de mamona. Documentos,* 134. Embrapa Algodão, Campina Grande, P B; Barnes D J, Baldwin B S, Braasch D A, 2009. Ricin accumulation and degradation during castor seed development and late germination. Ind Crops Prod 30:254-258; Bozza W P, Tolleson W H, Rosado L A R, Zhanga B, 2015. Ricin detection: Tracking active toxin. Biotechnol Adv 33:117-123). The presence of ricin may lead to the inactivation of ribosomes, cell organelles, being potentially lethal to animals, including human beings. The lethal doses for animals range from 0.1 g/kg for equines to 2.3 g/kg for swines (FONSECA; SOTO-BLANCO. Toxicity of ricin presente in castor bean seeds Semina: Ciências Agrárias, Londrina, v. 35, n. 3, p. 1415-1424. 2014). For humans, the consumption of five seeds can be lethal (OSNES, S. The history of ricin, abrin and related toxins. Toxicon, v. 44, n. 4, p. 361-370, 2004). The use of the cake as animal food requires its prior detoxification; however, the methods developed so far are poorly efficient and/or economically unfeasible in large scale (Severino L S, Auld D L, Baldanzi M, Cândido M J D, Chen G, Crosby W, Tan D, He X, Lakshmamma P, Lavanya C, Machado O L T, Mielke T, Milani M, Miller T D, Morris J B, Morse S A, Navas A A, Soares D J, Sofiatti V, Wang M L, Zanotto M D, Zieler H (2012) A review on the challenges for increased production of castor. Agron J 104:853-880).

As to the patent documents relating to the development of castor-oil plants without ricin, the scarce disclosures on the matter do not address obtaining castor-oil plants without ricin through molecular biology techniques. The documents from this field report an improved production of ricinucleic acid, as appears in the patent document WO200070052, that refers to a gene isolate from genomic of *Ricinus communis* encoding a protein able to interact with the enzyme oleate 12-hydroxylase. Nevertheless, as we assess patent documents aimed at obtaining detoxified castor-oil plants, we identify additional available technologies, as it is the case with detoxification processes of castor-oil seeds and cake (BR102015030887, CN103766598, CN103766599, CN103892145 and FR2940804).

As it is well known, there are several copies of the ricin gene inside the castor-oil plant genome (Chan A P, Crabtree J, Zhao Q, Lorenzi H, Orvis J, Puiu D, Melake-Berhan A, Jones K M, Redman J, Chen G, Cahoon E B, Gedil M, Stanke M, Haas B J, Wortman J R, Fraser-Liggett C M, Ravel J, Rabinowicz P D (2010) Draft genome sequence of the oilseed species *Ricinus communis. Nat Biotechnol* 28:951-956) and the amount of ricin depends on the variety (Baldoni A B, Araújo A C G, Carvalho M H, Gomes A C M M, Aragão FJL (2010) Immunolocalization of ricin accumulation during castor bean (*Ricinus communis* L.) seed development. Int J Plant Biol 1:61-65); but there is no report about the existence of ricin-free plant varieties.

The post-transcriptional gene silencing refers to the trans-activation of homologous genes due to RNA degradation. Although some works disclose the PTGS induction through single-copy inserts, the presence of inverted repetitions and multiple copies of transgenes is typically associated with silencing (as mentioned in the patent application US20030135888, Jorgensen et al., *Plant Mol. Biol.*, 31:957 (1996)). The ectopic pairing DNA-DNA or DNA-RNA, or the formation of anti-sense transcriptions giving rise to dsRNA is believed to result into formation of RNA aberrant transcriptions (including the loss of RNA polyadenylation or short RNA polyadenylation, generally resulting from incomplete transcription) that activate silencing (as mentioned in the patent application US20030135888, Baulcombe et al. *Curr. Opin. Biotechnol.*, 7:173 (1996); Depicker et al., *Curr. Opin. Cell Biol.*, 9:373 (1997); Metzlaff et al., *Cell*, 88:845 (1997); Montgomery et al., *Trends Genet.*, 14:255 (1998); Que et al., *Dev. Genet.*, 22:110 (1998); Stam et al., *Mol Cell Biol.*, 18: 6165 (1998); and Wassenegger et al., *Plant Mol. Biol.*, 37:349 (1998)). The simplest PTGS method with dsRNA involves a construct containing a nucleic acid sequence, or fragment thereof, that is oriented towards the promoter in a contrary sense, thus resulting into the formation of an anti-sense mRNA. This anti-sense mRNA, upon transcription inside the organism cell, shall complementarily bind to an endogenous mRNA molecule, thus leading to the formation of a double stranded mRNA molecule, that shall trigger a process involving various enzymes to the amplification of the response, with a consequent silencing of the mRNA-specific gene, or, in other words, a reduction or lack of the protein encoding such gene (U.S. Pat. No. 5,107,065, US20030135888, US20040216190).

A derived form of anti-sense technology consists in the insertion of gene constructs inside organisms containing nucleic acid sequences in both sense and anti-sense orientations separated by a spacing sequence, such as introns, that shall lead to the formation of a structure in the shape of artificial clip of double stranded mRNA. This technology, also referred to as RNA interference, was found to be much more efficient than the mere insertion of the nucleic acid molecule in anti-sense orientation, as the mRNA molecule does not need to find the complementary molecule. The use of RNA interference (RNAi) demonstrated the possibility of obtaining plants with indetectable levels of transcription, or with no level at all (Wesley S V, Heliwell C A, Smith N A, Wang M, Rouse D T, Liu Q, Gooding P S, Singh S P, Abbott D, Stoutjesdijk P A, Robinson S P, Cleave A P, Green A G & Waterhouse P M (2001) Construct design for efficient, effective and high-throughput gene silencing in plants, *The Plant Journal.* 27: 581-590, WO9953050, US20030175783, US20030180945, US20050120415), and thus appears as an efficient methodology for silencing ricin in plants.

Therefore, this invention presents a a novel matter with large industrial application, namely the production of free ricin/RCA toxin castor-oil plants obtained through post-transcriptional silencing of ricin genes.

SUMMARY OF THE INVENTION

This invention relates to a method for obtaining ricin/RCA free castor-oil plants through the insertion of gene constructs into vegetable cells, particularly castor-oil plants, thus resulting in the production of ricin/RCA free castor-oil plant seeds.

A first embodiment of the invention provides synthetic polynucleotide molecules comprising a first region containing a nucleic acid sequence showing at least 90% similarity with the sequence described in SEQ ID. No. 12, and a second region containing the complement of the sequence from the first one.

An additional embodiment provides a synthetic polynucleotide comprising a first region containing a nucleic acid sequence as described in the SEQ. ID. No. 12, a second region containing a nucleic acid sequence as described in the SEQ. ID. No. 13 and a spacing region between the first and the second ones, containing a nucleic acid sequence as described in the SEQ. ID. No. 5.

This invention also provides a gene construct comprising a synthetic polynucleotide comprising a first region containing a nucleic acid sequence with at least 90% similarity with the sequence as described in the SEQ. ID. No. 12, and a second region containing the complement of the sequence from the first region, as well as a region of active gene promoter operationally bound to the synthetic polynucleotide. A vector containing said gene construct is also provided.

Additionally, this invention provides a vector comprising a gene promoter according to the sequence described in the SEQ. ID. No. 4, a first region encoding a nucleic acid sequence as described in the SEQ. Id. No. 12, a second region encoding a nucleic acid sequence according to the sequence described in the SEQ. ID. No. 13, a spacing region between the first and the second ones, containing a nucleic acid sequence as described in the SEQ. ID. No. 5, and end signal according to the sequence described in the SEQ. ID. No. 6, a marker gene comprising the promoter as described in the SEQ. ID. No. 7, a coding region as described in the SEQ. ID. No; 8 and an end signal as described in the SEQ. ID. No. 9, and a selection gene comprising the promoter as described in the SEQ. ID. No. 1, a coding region described in the SEQ. ID. No. 2, and an end signal described in the SEQ. ID. No. 3.

In another embodiment, the invention provides a double-helical filament molecule of ribonucleotide, produced by the expression of any of the previously mentioned nucleotide molecules.

This document also provides a method for obtaining ricin/RCA free castor-oil plants comprising the steps of:
a. inserting any of the aforesaid nucleic acid molecules into castor-oil plant cells;
b. cultivating or regenerating the cells in specific means; and
c. selecting the plants with the silenced ricin gene.

This invention also provides an eukaryotic cell and plant comprising any of the aforesaid nucleic acid molecules. The plant seed is also provided.

Another embodiment refers to the method to the identification of the genetically modified plant, and comprises the steps of:
a. forming a mix comprising a biological sample containing castor-oil plant DNA, and a pair of primers able to amplify a specific nucleic acid from a genetically modified ricin/RCA free castor-oil plant;
b. reacting to the mix under conditions that allow the pair of nucleic acid primers to amplify a specific nucleic acid molecule from a genetically modified ricin/RCA free castor-oil plant;

c. detecting the presence of a specific amplified nucleic acid molecule from a genetically modified ricin/RCA free castor-oil plant.

The invention also provides a kit to identify nucleic acid molecules of castor-oil plant from a biological sample comprising a pair of nucleic acid primers selected among the following pairs: SEQ ID NO 19 with SEQ ID NO 20, SEQ ID NO 21 with SEQ ID NO 22, SEQ ID NO 23 with SEQ ID NO 24 or SEQ ID NO 25 with SEQ ID NO 26.

This invention also provides a method for obtaining a ricin/RCA free castor-oil plant, comprising the steps of:
I. breeding a castor-oil plant containing a nucleic acid molecule from the TB14S-5D event with a second castor-oil plant;
II. obtaining seeds from the breeding as described in the step I;
III. obtaining a sample from the seed DNA, and
IV. detecting the presence of a nucleic acid molecule from the event TB14S-5D of the castor-oil plant.

Finally, this invention provides castor oil extracted from transgenic seed, as well as the castor seed cake obtained by using transgenic seed.

BRIEF DESCRIPTION OF THE FIGURES

FIG. 4—Northern blot shows the presence of siRNAs (small RNAs) and the absence of ricin gene transcript in the event TB14S-5D (+). In contrast, no sRNA was observed, and the ricin gene transcript was present in NT plants, or negative segregants of the event TB14S-5D (−).

Figure 5:
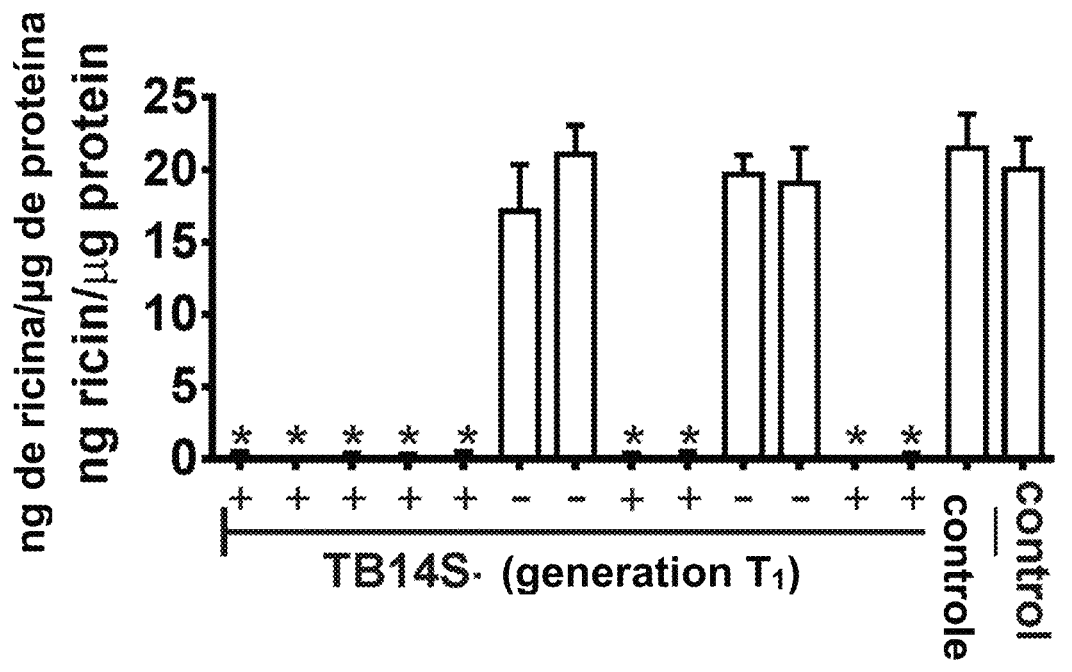

FIG. 5—Detection of ricin silencing in the event TB14S-5D. An ELISA test was performed to identify and quantify ricin in the endosperm of the event TB14S-5D seeds. Ricin was detected in the endosperm of non-transgenic seeds, as well as in the negative segregating seeds. However, ricin was not detected in positive seeds from the event TB14S-5D.

FIG. 7—PCR analysis showing the presence of fragments resulting from amplification of a fragment corresponding to a sequence of the interference cassette (Δricin). NT is a non-transgenic plant, and pRIcRNAi is the vector used in the gene modification of castor-oil plant.

DETAILED DESCRIPTION OF THE INVENTION

Figure 1:
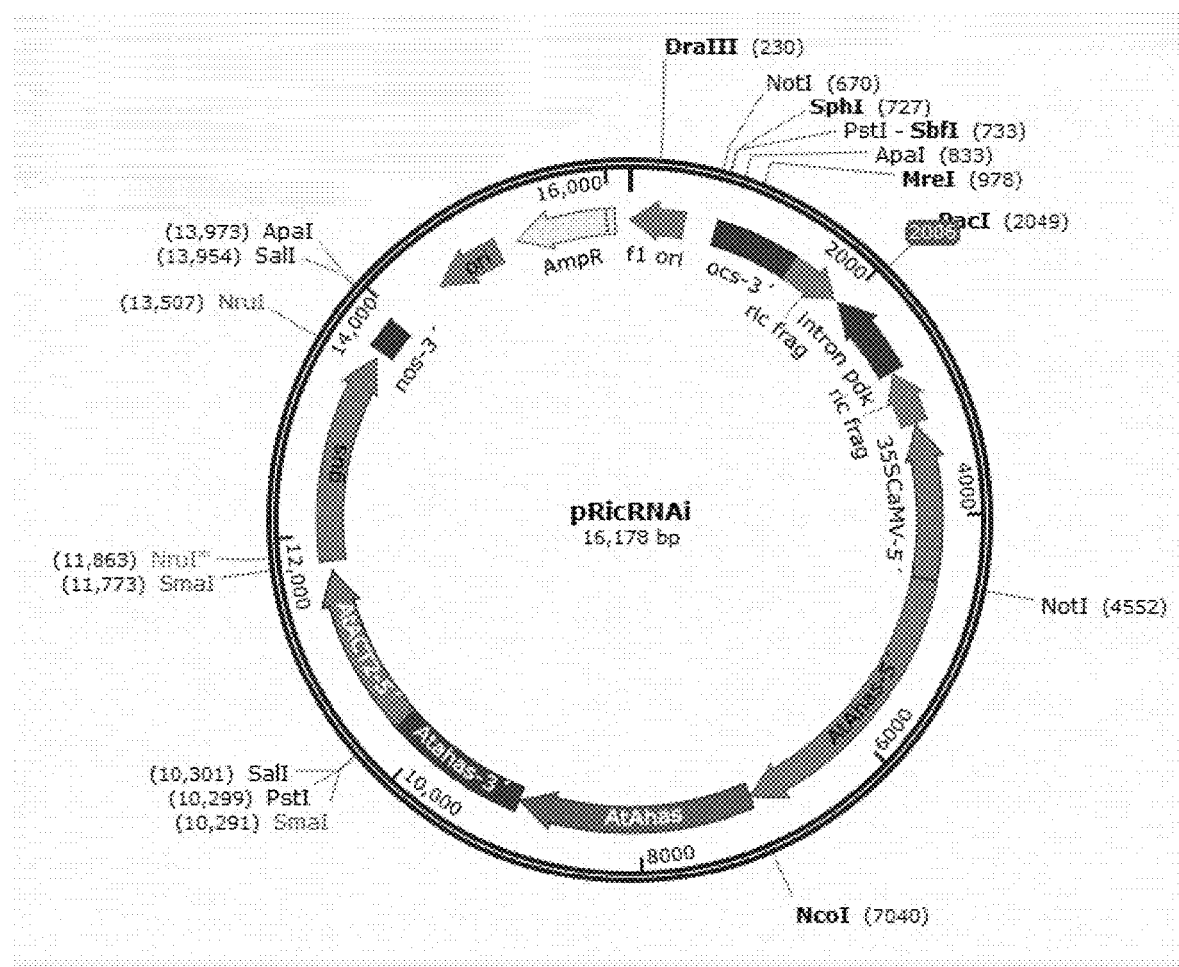
FIG. 1—A representation scheme of construct used to the transformation of the castor-oil plant. Vector for pRicRNAi biolistic composed by a transformation cassette, a fragment of ricin (ric) gene in sense and anti-sense interlayed by an intron, under the control of a promoter 35SCaMV and a terminator OCS, the ahas (AtAhas) gene and the gus gene driven by the promoter AtACT2.

This invention addresses the production of ricin/RCA toxin free castor-oil plants, obtained through the post-transcriptional ricin gene silencing.

Within the context of this specification, several terms used herein are defined as follows.

The term "nucleic acid" refers to a large molecule that can be either single or double stranded, composed of monomers (nucleotides) containing a sugar, a phosphate and a purine or pyrimidine base. A "nucleic acid fragment" is a fraction of a certain nucleic acid molecule. "Complementarity" refers to the specific pairing of purine and pyrimidine bases composed of nucleic acids: adenine and thymine pairs and guanine and cytosine pairs. So, the "complement" of a first nucleic acid fragment refers to the second nucleic acid fragment whose nucleotide sequence is complementary to the first nucleotide sequence.

In more developed plants, the deoxyribonucleic acid (DNA) is a gene material, while ribonucleic acid (RNA) is involved with information transfer from the DNA into proteins. A "genome" is the whole major portion of gene material contained in each cell of an organism. The term "nucleotide sequence" refers to nucleotide polymer sequences forming a DNA or RNA in a single or double strand, optionally synthetic, non-natural, or containing altered nucleotide bases with ability to incorporate inside DNA or RNA polymers. The term "oligomer" refers to short nucleotide sequences, usually up to 100 base-long. The term "homologous" refers to the bond between nucleotide sequences with two nucleic acid molecules, or between amino acid sequences with two protein molecules. An estimate of such homology is provided through hybridization of DNA-DNA or RNA-RNA under stringency conditions, as defined by the state of art (as mentioned in the document US20030074685, Hames and Higgins, Ed. (1985) Nucleic Acid Hybridization, IRL Press, Oxford, U.K); or by comparing the sequence similarity between two nucleic acid molecules or proteins (as mentioned in the document US20030074685, Needleman et al., J. Mol. Biol. (1970) 48:443-453).

"Gene" refers to the nucleotide fragment expressing a specific protein, including precedent (non-translated locus 5') and posterior (non-translated locus 3') regulatory sequences to the coding region. "Native gene" refers to a gene isolated from its own regulatory sequence found in the nature. "Chimeric gene" refers to the gene that comprises coding, regulatory and heterogeneous sequences not found in the nature. "Endogenous gene" refers to a native gene, usually found in its natural location inside the genome, that is not isolated. An "exogenous gene" refers to a gene that is not usually found in the host organism, being, instead, introduced there through gene transfer. "Pseudogene" refers to a nucleotide sequence that does not encode a functional enzyme.

"Coding sequence" refers to the DNA sequence that encodes a specific protein and excludes the non-coding sequence. An "interrupted coding sequence" means a sequence that acts as a separator (for instance, one or more introns binding through junctions).

An "intron" or "spacing region" is a nucleotide sequence transcript and present in the pre-mRNA, but that is removed through cleavage and re-connection of mRNA inside the cell, thus generating a mature mRNA that can be translated into a protein. Examples of introns include, but are not limited to pdk, pdk2 intron, castor bean catalase intron, delta 12 desaturase intron (cotton), delta 12 desaturase (*Arabidopsis*), maize ubiquitin intron, SV40 intron, ricin gene introns. This invention used the pdk intron (SEQ. ID. No. 5).

"RNA Transcript" refers to the product resulting from the catalyzed transcription of a DNA sequence by RNA polymerase. Whenever the RNA transcript is a perfect copy of the DNA sequence, it is referred to as primary transcript, or may be a RNA sequence derived from a post-transcriptional process of the primary transcript, being thus referred to as mature transcript. "Messenger RNA (mRNA)" refers to the RNA deprived of introns. "RNA sense" refers to a RNA transcript including mRNA. "RNA anti-sense" refers to a RNA transcript that is complementary to all the portions of a primary transcript or mRNA, and that is able to block a target gene expression through interfering in the process, transport and/or translation of its primary transcript or mRNA. The complementarity of a RNA anti-sense can be identified with any portion of the specific gene transcript, namely the non-translated sequence 5', the non-translated sequence 3', introns or coding sequence. Additionally, the RNA anti-sense may contain regions with ribozyme sequences that improve the effectiveness of RNA anti-sense to block the gene expression. "Ribozyme" refers to the catalyctic RNA and encompasses sequence-specific endoribonuclease. "DsRNA (double stranded RNA)" refers to the clip structure formed between the mRNA sequence or RNA sense, the sequence of a specing/intron region, and the RNA anti-sense sequence.

The term "similarity" refers to nucleic acid fragments where changes in one or more nucleotide bases do not affect the nucleic acid fragment's ability to mediate the alteration of the gene expression by gene silencing, such as, for instance, by using the anti-sense technology, the co-suppression or RNA interference (RNAi). Similar nucleic acid fragments herein can also be characterized by the percentage of similarity between their nucleotide sequences and the nucleotide sequences of nucleic acid fragments described herein (SEQ. ID. No. 12 and SEQ. ID. No. 13), as determined by ordinary algorithms employed by the state of art. The sequence alignment and the calculation of similarity percentage herein were performed by the DNAMAN Program for Windows (Lynnon Corporation, 2001), by using sequences filed in the Gene Bank through the Web browser integration. For this invention, it is possible to use other A channel regions with similar effect, as well as B channel sequences, but, in this latter case, with effect on RCA/RCA120 (*Ricinus communis* agglutinin).

The formation of dsRNA requires the presence, inside the DNA molecule, of a target gene nucleotide sequence in the sense orientation, and a nucleotide sequence in the anti-sense orientation, with or without a spacing/intron region between the sense and anti-sense nucleotide sequences. Said nucleotide sequences can be formed from about 19nt to 470 nt, or about 1740 nucleotides or more, provided that each one keeps a substantial similarity of total sequence from about 40% to 100%. The longer shall be the sequence, the lower shall be the stringency required to the total substantial similarity of the sequence. The fragments containing at least 19 nucleotides should preferably show about 90%, 91%, 92%, 93%, 94%, 95%, 96%, 97%, 98% or 99% identity of sequence, when compared to the reference sequence, with the possibility of containing about 2 different non-contiguous nucleotides. Fragment above 60 pb are preferably used, and still more preferably from 150 to 500 pb.

In one aspect of the invention, the dsRNA molecule may comprise one or more regions showing substantial sequence similarity for regions containing at least about 14 nucleotides consecutive to the target gene sense nucleotides defined as first region, and one or more regions showing substantial sequence similarity for regions containing about 15 nucleotides consecutive to the complement of target gene sense nucleotides, defined as second region, where such regions may present pairs of bases to separate them from each other. This invention used fragments of 461 nucleotides (SEQ. ID. No. 12 and SEQ. ID. No. 13) from the ricin gene of the castor-oil plant.

For convenience sake, the double stranded RNA (dsRNA) as described can be expressed in host cells, from a gene construct introduced and possibly integrated to the host cell's genome. So, in one embodiment, the invention refers to a synthetic polynucleotide comprising: a first region containing nucleic acid sequence showing at least 90, 95, 99 or 100% similarity with the sequence described in the SEQ. ID. No. 12, and a second region containing the complement of the sequence from the first region. Such polynucleotide may present a specing region between the first and the second ones; this spacing region may be an intron sequence selected among: pdk intron (SEQ. ID. No. 5), pdk2 intron, castor bean catalase intron, delta 12 desaturase intron (cotton), delta 12 desaturase (*Arabidopsis*), maize ubiquitin intron, SV40 intron, ricin gene introns.

"Promoter" refers to the DNA sequence in one gene, usually located upstream the coding sequence, that controls the coding sequence expression by promoting recognition by RNA polymerase and other factors required for the transcription itself. In the construct of an artificial DNA, promoters can also be used for the transcription of dsRNA. Promoters may also contain DNA sequences involved with binding protein factors that control the effect of the early transcription in response to physiological or development conditions.

In one of the embodiments, the invention provides a gene construct comprising the previously characterized polynucleotide and a region of the active gene promoter operationally bound to said polynucleotide.

Such promoter can be a promoter expressed in plants. As used herein, the term "promoter expressed in plants" means a DNA sequence that is able to start and/or control the transcription in a plant cell. This includes any vegetable promoter, any non-vegetable promoter that is able to direct the expression in a vegetable cell, such as, for instance, viral or bacterial promoters such as CaMV35S (as mentioned in the patent application patent US20030175783, Hapster et al, 1988 Mol. Gen. Genet. 212, 182-190) and gene promoters present in the T-DNA of *Agrobacterium*; tissue-specific or organ-specific promoters, including, but not limited to specific seed promoters (WO8903887), specific primary organs promoters (as mentioned in the patent application US20030175783, An et al., 1996 The Plant Cell 8, 15-30), stem-specific promoters (as mentioned in the patent application US20030175783, Keller et al., 1988 EMBO J. 7: 3625-3633), leave-specific promoters (as mentioned in the patent application US20030175783, Hudspeth et al., 1989 Plant Mol Biol 12:579-589), mesophyll-specific promoters, root-specific promoters (as mentioned in the patent application US20030175783, Keller et al., 1989 Genes Devel. 3:1639-1646), tuber-specific promoters (as mentioned in the patent application US20030175783, Keil et al., 1989 EMBO J. 8: 1323:1330), vascular tissue-specific promoters (as mentioned in the patent application US20030175783, Peleman et al., 1989 Gene 84: 359-369), stamen-specific promoters (WO8910396, WO9213956), dehiscence zone-specific promoters (WO9713865); and the like. This invention preferably used the following promoters: 1) Promoter of the Ahas gene from *Arabidopsis thaliana* that drives the ahas gene expression (pAtAhas—SEQ ID NO 1); 2) Constitutive promoter CaMV35S that drives the expression of K7 from RNAi to the ricin fragment (pCaMV35S—SEQ ID NO 4) and 3) Constitutive promoter of the Actin 2 gene from *Arabidopsis thaliana* that drives the gus gene expression (pAtAct2—SEQ ID NO 7).

The promoter may contain "enhancer" elements. An enhancer is a DNA sequence that can stimulate the promoter's activity. It can be an innate element from the promoter, or a heterologous element inserted to increase the level and/or the tissue-specificity of a promoter. This invention used the enhancer sequence of Alfalfa mosaic virus (35SCaMV).

"Constitutive promoters" refer to the ones that drive the gene expression in all the tissues and during the whole time. "Tissue-specific" or "development-specific" promoters are the ones that drive the gene expression almost exclusively in specific tissues, such as leaves, roots, stems, flowers, fruits, or seeds, or at specific development steps in a tissue, such as at the beginning and at the end of embryogenesis. The term "expression" refers to the transcription and stable accumulation of nucleic acid fragment-derived RNA of the invention that, together with the protein production structure of the cell results into altered levels of mio-inositol 1-phosphate synthase. "inhibition by interference" refers to the production of dsRNA transcripts that can prevent the target protein expression.

"Termination signal" or "terminators" are sequences that orientate the RNA polymerase enzyme to stop RNA transcription. The termination signal of transcription/terminators herein include, but are not limited to a SV40 termination signal, adenylation signal of HSV TK, termination signal of nopalyn synthetase from *Agrobacterium tumefaciens* (nos), termination signal of the gene RNA 35S from CaMV, termination signal of the virus that attacks *Trifolium subterranean* (SCSV), termination signal of the gene trpC from *Aspergillus nidulans*, and the like. This invention preferably used the following "termination signals" or "terminators": 1) Terminator sequence of Ahas-3' gene from *Arabidopsis thaliana* (SEQ ID NO 3); 2) Terminator sequence ocs-3' that ends the expression of K7 from RNAi Ric (SEQ ID NO 6); and 3) Terminator sequence nos-3' that ends the transcription of the gus reporter gene or uidA (SEQ ID NO 9).

"Appropriate regulatory sequences" refer to nucleotide sequences in native or chimeric genes, located above (non-translated region 5'), inside and/or below (non-translated region 3') the nucleic acid fragments of the invention, that control the expression of nucleic acid fragments herein.

"Altered levels" refer to the production of gene products in transgenic organisms, in amounts or proportions that differ from the ones observed in normal or non-transgenic organisms. This invention also discloses vectors/gene constructs that include sequence fragments of ricin gene from the castor-oil plant in sense and anti-sense orientation, as well as host cells, that are genetically engineered with vectors of this invention. "Transformation" refers to the transfer of an exogenous gene into the genome of a host organism, and its genetically stable heritage.

Plants refer to photosynthetic and eucaroitic organisms. The nucleic acids of the invention can be used to provide desired traits basically in any plant. So, the invention can be used for several plant species, including the following genus: *Anacardium, Anona, Arachis, Artocarpus, Asparagus, Atropa, Avena, Brassica, Carica, Citrus, Citrullus, Capsicum, Carthamus, Cocos, Coffee, Cucumis, Cucurbita, Daucus, Elaeis, Fragaria, Glycine, Gossypium, Helianthus, Heterocallis, Hordeum, Hyoseyamus, Lactuca, Linum, Lolium, Lupinus, Lycopersicon, Malus, Manihot, Majorana, Medicago, Nicotiana, Olea, Oryza, Panieum, Pannesetum, Passiflora, Persea, Phaseolus, Pistachia, Pisum, Pyrus, Prunus, Psidium, Raphanus, Ricinus, Secale, Senecio, Sinapis, Solanum, Sorghum, Theobromus, Trigonella, Triticum, Vicia, Vitis, Vigna,* and *Zea.* Plants from the genus *Ricinus* were preferably used in this invention. More specifically, this invention refers to *Ricinus communis* plants.

Another object of this invention is to provide eukaryotic cells and eukaryotic organisms containing dsRNA of the invention, or gene constructs that are able to produce dsRNA of the invention. These gene constructs can be stably integrated in the genome of cells from eukaryotic organisms.

In another embodiment, the gene constructs can be provided in a DNA molecule that is able to replicate, on an autonomous basis, inside the cells of eukaryotic organisms, such as viral vectors. This invention used a sequence originated from the replication of Plasmidium from pKannibal (SEQ ID NO 10). The chimeric gene, or dsRNA can be also arranged on a transient basis inside the cells of eukaryotic organisms.

The gene constructs of this invention still present coding sequences for selection and marker genes to assist in the recovery process of the transgenic event. Several marker and selection genes can be used in this invention, including, but not limited to: nptll, hpt, neo, bar, ahas, epsps. This invention preferably used: 1) coding gene sequence of the Ahas gene from *Arabidopsis thaliana* (SEQ ID NO 2); 2) gus reporter gene sequence or uidA (SEQ ID NO 8); and 3) gene sequence of resistance to ampicillin from the *plasmodium* of pKannibal (SEQ ID NO 11).

An embodiment of the invention refers to a vector for plant transformation, comprising:
  Gene promoter according to the sequence described in SEQ. ID. No. 4;
  A first coding region containing nucleic acid sequence according to the sequence described in SEQ. ID. No. 12;
  A second coding region containing nucleic acid sequence according to the sequence described in SEQ. ID. No. 13;
  A spacing region between the first and the second ones, containing nucleic acid sequence according to the sequence described in SEQ. ID. No. 5;
  Termination signal according to the sequence described in SEQ. ID. No. 6;
  Marker gene comprising the promoter described in the SEQ. ID. No. 7, a coding region described in the SEQ. ID. No. 8 and a termination signal described in the SEQ. ID. No. 9;
  Selection gene comprising the promoter described in the SEQ ID. No. 1, an encoding region described in the SEQ. ID. No. 2, and a termination signal described in the SEQ. ID. No. 3.

The polynucleotides, gene constructs and vectors of the invention can be introduced into the genome of a desired host plant through a variety of conventional techniques. For instance, they can be directly introduced into the genomic DNA of a vegetable cell by using techniques, such as electroporation and micro-injection of protoplasts of plant cells, or the construct can be directly introduced into a vegetable tissue, by using ballistic methods, such as bombing particles covered with DNA.

Micro-injection techniques are known from the state of art, being well described by the scientific and patent literature. The introduction of gene constructs by using glycol polyethylene precipitates is described by Paszkowski et al. Embo J. 3:2717-2722, 1984 (as mentioned in the patent application US20020152501). Electroporation techniques are described in From et al. Proc. Natl. Acad. Sci. USA 82:5824, 1985 (as mentioned in the patent application US20020152501). Ballistic transformation techniques are described in Klein et al. Nature 327:70-73, 1987 (as mentioned in the patent application US20020152501).

Alternatively, the gene constructs can be combined with flanking regions of appropriate T-DNA and introduced into a conventional vector inside the host *Agrobacterium tumefaciens*. The virulence of the host *Agrobacterium tumefaciens* shall drive the insertion of gene constructs and adjacent marker inside the DNA of the vegetable cell, as soon as the cell is infected by bacteria. Transformation techniques mediated by *Agrobacterium tumefaciens*, including disarming and the use of binary vectors are well described by the scientific literature (as mentioned in the patent application US 20020152501, Horsch et al. Science 233:496-498, 1984; and Fraley et al. Proc. Natl. Acad. Sci. USA 80:4803, 1983). This invention preferably used the biobalistic technique. Nevertheless, genetically modified castor-oil plants can be obtained from *A. tumefaciens*.

Transformed plant cells derived from any of the transformation techniques described above can be cultured to regenerate a whole plant transformed in its genotype, thus reaching the desired phenotype, such as lack or reduction in the seed mass. Such regeneration techniques rely upon the manipulation of certain phytohormones in tissue culture mean, typically containing a biocide and/or herbicide marker to be introduced together with the desired nucleotide sequence. Plant regeneration from a culture of protoplasts is described by Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985 (as mentioned in the patent application US20020152501). The regeneration can also be achieved through plant callus, explants, organs, or parts thereof. Such regeneration techniques are generally described in Klee et al., Ann. Ver. Of Plant Phys. 38:467-486, 1987 1985 (as mentioned in the patent application US20020152501).

Therefore, this invention refers to a method for obtaining ricin/RCA-free castor-oil plants, characterized by the fact that it comprises the steps of:

a. inserting into castor-oil plant cells the aforesaid nucleic acid molecule, that can be a polynucleotide, a gene construct, a vector or double filament ribonucleotide as previously defined;
b. culturing or regenerating castor-oil plant cells in specific means;
c. selecting the castor-oil plants containing the silenced ricin gene.

Without limiting the invention to a certain kind of action, the enzyme present in eukaryotic cells and responsible for generating small RNA molecules such as DICER in *Drosophila* is expected to be saturated through the inclusion of an exceeding amount of dsRNA sequences (double stranded RNA molecules), that are not related to the target gene nucleotide sequence, or to be gene to be silenced.

The natural variation in the posterior regulation of the target gene expression (that occurs between different lineages of eukaryotic organisms comprising the same dsRNA molecule) shall be replaced with the manipulation of the gene silencing spectrum. This result can be achieved through inclusion of nucleotide sequences of additional dsRNA non-related to the target gene, that are operationally bound to the dsRNA formed by the first and the second regions.

The invention also concerns the use of double filament ribonucleotide molecule of this invention to the suppression of ricin/RCA gene expression.

In another embodiment, the invention provides a method to identify transgenic free ricin/RCA castor-oil plants, comprising the steps of:

a. forming a mixture that comprises a biological sample containing castor-oil plant DNA and a pair of primers able to amplify a specific nucleic acid molecule from a genetically modified ricin/RCA free castor-oil plant;
b. reacting to the mix under conditions that enable the pair of nucleic acid primers to amplify a specific nucleic acid molecule from a genetically modified ricin/RCA free castor-oil plant;
c. detecting the presence of the specific amplified nucleic acid molecule from a genetically modified ricin/RCA free castor-oil plant.

The primers used in the identification of the transgenic castor-oil plant are described in the table 1.

TABLE 1 pairs of primers used in the identification of genetically modified ricin/RCA free castor-oil plant:

| Function/target of the pair of primers | Primer | SEQ ID NO | Sequence | Resulting fragment |
|---|---|---|---|---|
| Interference cassette Δricin | PSIUINTF | 19 | GAACCCAATTTCCCAACTG | 798 pb |
| | PSIUINTR | 20 | AGGTACCCCAATTGGTAAGGA | |
| Ricin gene sequence (A channel) | RcRinR | 21 | GAAGCTTGGTACCTAATTCTCGTGCGCAT | 460 pb |
| | RcRinf | 22 | GTCTAGACTCGAGACATGAAATACCAGTGTTGC | |
| Specific marker of the event TB14S-5D | AHASCD2F | 25 | TATTCTTCCCAATCTCAGCC | 396 pb (SEQ ID NO 27) |
| | SOJAE1R | 26 | CCTCGGGATTTGATTTTTGGTCCT | |

In another embodiment, the invention also comprises a kit for identification of a nucleic acid molecule of the event TB14S-5D from castor-oil plant in a biological sample comprising a pair of nucleic acid primers selected among the following pairs: SEQ ID NO 19 and SEQ ID NO 20, SEQ ID NO 21 and SEQ ID NO 22, SEQ ID NO 23 and SEQ ID NO 24 or SEQ ID NO 25 and SEQ ID NO 26, that are able to amplify a nucleic acid molecule from the event TB14S-5D of castor-oil plant, provided that this amplified molecule can be the sequence presented in SEQ. ID. No. 27.

This invention also provides a method for obtaining a ricin/RCA free castor-oil plant, characterized by the steps of:

1. breeding a castor-oil plant containing a nucleic acid molecule of the event TB14S-5D and a second castor-oil plant;
2. obtaining seeds from the breeding described in the step (a);
3. obtaining a DNA sample of the seed; and
4. detecting the presence of nucleic acid molecule in the event TB14S-5D of the castor-oil plant.

Finally, this invention provides castor oil extracted from transgenic seeds of transformed plants, comprising the nucleic acid molecules provided and the castor-oil plant cake obtained through a process that also uses such seeds.

The various experiments performed to check the presence/absence of ricin are described in the examples herein. While the endosperms of genetically modified seeds were used in the tests of hemagglutination and survival of epithelial cells of mouse gut (IEC-6), the embryonary axis (T1) were cultured in vitro, and then transferred into vegetation houses. Additionally, the GM plants presented a strong histochemical GUS activity, that made leaves, endosperms and embryonary axis notably blue within 20 minutes. The use of such marker shall be very useful to determine, even under field conditions, if a specific variety is genetically modified. This will be relevant to the safe use of GM varieties in animal nutrition, as the use of varieties containing ricin is lethal.

EXAMPLES

The full sequence of gene construct used herein is described in the SEQ. ID. No. 14, and any person skilled in the art shall be able to synthetize this sequence to insert it into the desired eukaryotic organism.

This invention is still defined in the following Examples. It must be clearly understood that these Examples, while indicating part of the invention, are only referred to for illustration purpose, and do not limit the scope herein.

Usual molecular biology techniques, such as bacterial transformation and electrophoresis in agarose gel of nucleic acids are referred to by ordinary terms used to describe them. Practical well-known details about these techniques are described by the state of art in Sambrook, et al. (Molecular Cloning, A Laboratory Manual, $2^{nd}$ ed. (1989), Cold Spring Harbor Laboratory Press). Several solutions used in experimental manipulations are referred to by their ordinary designations, such as “lysis solution”, “SSC”, “SDS”, etc. The compositions of such solutions can be found in the aforesaid reference Sambrook, et al.

Example 1

Building Vectors to the Gene Transformation of Castor-Oil Plants

The vector was built by using a RcRCAI gene fragment (SEQ ID NO 12,—sense and SEQ ID NO 13—anti-sense) that encodes the ricin A channel highly similar to RCA 120, as the A channel is responsible for the toxicity.

The whole DNA was isolated from fresh tissues of castor-oil plants by using the DNeasy Plant Mini Kit (Qiagen, Valencia, CA, USA), and PCR reactions were performed to clone the RcRCAI gene by using the primers RcRINF (5'-GTCTAGACTCGAGACATGAAATACCAGTGTTGC-3') SEQ ID NO: 22) and RcRINR (5'-GAAGCTTGGTACCTAATTCTCGTGCGCAT-3') SEQ ID NO: 21) added with sites of KpnI/XhoI and HindIII/XbaI enzymes at the end of each one. The amplified fragment of about 480 pb was cloned in the vector pGEM-TEasy (Kobs, G. (1997) Cloning blunt-end DNA fragments into the pGEM®-T Vector Systems. Promega Notes 62, 15-18). Then, the intron-hairpin-type construct was performed through insertion of the fragment from RcRCAI gene in the sense (SEQ. ID. No. 12) and anti-sense (SEQ. ID. No. 12) orientations in the pKANNIBAL vector (Wesley, S., Helliwell, C., Smith, N., Wang, M., Rouse, D., Liu, Q., Gooding, P., Singh, S., Abbott, D., Stoutjesdijk, P., Robinson, S., Gleave, A., Green, A., and Waterhouse, P. 2001. Construct design for efficient, effective and high-throughput gene silencing in plants. Plant J. 27:581-590), being separated by PDK intron (SEQ. ID. No. 5) under the promoter domain 35SCaMV (SEQ ID NO 4) and with the OCS terminator (SEQ. ID. No. 6), thus allowing the stranded RNA expression as source of generation of interfering RNAs. The transformation cassette (Promoter 35SKaMV—ricin fragment in the sense orientation—intron—ricin fragment in the anti-sense orientation—OCS terminator) was removed from pKANNIBAL vector in the site Nott, and inserted into the vector pAG1 (Aragão, F. J. L., Sarokin, L., Vianna, G. R., and Rech, E. L. 2000. Selection of transgenic meristematic cells utilizing a herbicidal molecule results in the recovery of fertile transgenic soybean (*Glycine max* (L.) Merrill) plants at high frequency. Theor. Appl. Genet. 101:1-6) that contains the gus gene (β-Glucuronidase-uidA) as reporter gene and the ahas gene as selection gene, thus forming the vector/gene construct pRICRNAi. (FIG. 1, SEQ ID NO 14). The gus reporter gene expression (SEQ. ID. No. 8) is regulated, in this construct, by the constitutive promoter of Actin 2 gene from *Arabidopsis thaliana* (SEQ ID NO 7) and by the terminator nos-3' (SEQ ID NO 9). On its turn, the ahas selection gene (SEQ ID NO 2) is regulated by the promoter of the Ahas gene from *Arabidopsis thaliana* and by the terminator of the Ahas-3' gene from *Arabidopsis thaliana* (SEQ ID NO 3).

Example 2

Transformation of Castor-Oil Plants

The methodology for obtaining genetically modified lineages of castor-oil plants was developed from the bombing of particles in meristematic regions of zygotic embryons of castor-oil plants.

Healthy seeds from the cultivar EBDA-MPA-34 were selected and disinfected through washing in alcohol 70% for 1 minute, followed by washing at 2% sodium hypochlorite added with Tween 20 (20 μL for each 100 mL solution) for 20 minutes. The method described herein is not limited to the variety EBDA-MPA-34 (as other varieties can be used with similar results). The seeds were washed 4 times with distilled autoclaved water and were left soaking for 24 hours. Then, the see tegument was broken with pliers, and the zygotic embryons were removed with a clamp and left in water to avoid dehydration. The embryons were washed three times with distilled autoclavated water, disinfected in sodium hypochlorite 0.5% for 10 minutes, and washed five times with autoclaved distilled water; then, the water in excess was removed, and the embryons were placed in early induction mean containing MS (Murashige and Skoog basal medium—Sigma M5519) added with casein 300 mg L−1, thyamine 100 mg L−1, 3% sacarose, indol-butyric acid IBA 0.05 mg L−1, thidiazuron (TDZ) 0.5 mg·L−1, 1.4% agar and pH 4.0, where they stayed for 48 hours in the incubator at 28° C. in the dark.

Upon expiry of this period, the merysteme of embryons was exposed through removal of cotiledones and leaf primordia with a scalpel, and they were once more inserted into MII mean, for 24 hours before the transformation.

The zygotic embryons of castor-oil plant with exposed merysteme were placed in a bombing mean containing MS (Murashige and Skoog basal medium—Sigma M5519) 0.5× added with 3% sacarose, 0.8% phyragel and pH 5.8, so that the merysteme was placed upwards, and the gene transformation by biobalistic was performed according to Aragão et al. 2000 (Aragão, F. J. L., Sarokin, L., Vianna, G. R., and Rech, E. L. 2000. Selection of transgenic meristematic cells utilizing a herbicidal molecule results in the recovery of fertile transgenic soybean (*Glycine max* (L.) Merrill) plants at high frequency. Theor. Appl. Genet. 101:1-6).

According to histological and anatomic analysis of explants induced and cultured in culture means, before and after gene transformation to allow the view of cell layers from the zygotic embryon's apical merysteme under transformation process, competent cells for gene transformation and regeneration were introduced into specific culture means to the generation of other yolks, thus obtaining transgenic sprouts. The second inconvenient of the process was the in vitro rooting of transgenic sprouts that was induced, and thus allowed obtaining a whole GM plant from the transfer of transgenes to its descendants.

Therefore, after the transformation, the embryons were once more transferred into a MII mean where they stayed for 24 hours, and then transferred into the induction and selection mean MIS containing MS (Murashige and Skoog basal medium—Sigma M5519) added with inositol 100 mg·L$^{-1}$, casein 300 mg·L$^{-1}$, thyamine 100 mg·L$^{-1}$, sacarose 3%, AIB 0.05 mg·L$^{-1}$, TDZ 0.5 mg·L$^{-1}$, imazapyr 150 nM, agar 1.4% and pH 4.0, where they stayed for seven days. Upon expiry of this period, the explants were transferred into a maintenance mean of multi-sprout and selection (MMM) containing MS (Murashige and Skoog basal medium—Sigma M5519) added with inositol 100 mg·L$^{-1}$, casein 300 mg·L$^{-1}$, thyamine 100 mg·L$^{-1}$, sacarose 3%, AIB 0.1 mg·L$^{-1}$, zeatin 1 mg·L$^{-1}$, imazapyr 150 nM, agar 1.4% and pH 4.0 for 15 days. Upon expiry of this period, the sprouts were separated and transferred into a sprout stretching mean (MAB) containing MS (Murashige and Skoog basal medium—Sigma M5519) added with inositol 100 mg·L$^{-1}$, casein 300 mg·L$^{-1}$, thyamine 100 mg·L$^{-1}$, sacarose 3%, AIB 1 mg·L$^{-1}$, giberetic acid (GA3) 1 mg·L$^{-1}$, silver nitrate 5 µM, imazapyr 200 nM, agar 1.4% and pH 4.0 and kept under streaking at each 15-day period, until appearance of well structured and stretched explants of about 2-3 cm, that were transferred into a rooting mean containing MS (Murashige and Skoog basal medium—Sigma M5519) added with inositol 100 mg·L$^{-1}$, casein 300 mg·L$^{-1}$, thyamine 100 mg·L$^{-1}$, sacarose 3%, AIB 2 mg·L$^{-1}$, giberelic acid (GA3) 0.5 mg·L$^{-1}$, silver nitrate 5 µM, agar 1.4% and pH 4.0. Plantules with about 3-4 cm and roots were acclimatized in vegetation house, in 700 mL glasses containing soil and vermiculite (1:1) with a plastic bag to keep moisture. Once acclimatized, the plants were transferred into a 8 L pot containing soil.

Example 3

Regeneration of Castor-Oil Plants

After the transformation, the embryons were once more transferred into MII mean where they stayed for 24 hours, and then transferred into the induction and selection mean MIS containing MS (Murashige and Skoog basal medium—Sigma M5519) added with inositol 100 mg·L−1, casein 300 mg·L−1, thyamine 100 mg·L−1, sacarose 3%, AIB 0.05 mg·L−1, TDZ 0.5 mg·L−1, imazapyr 150 nM, agar 1.4% and pH 4.0 where they stayed for seven days. Upon expiry of this period, the explants were transferred into a maintenance mean of multi-sprout and selection containing MS (Murashige and Skoog basal medium—Sigma M5519) added with inositol 100 mg·L−1, casein 300 mg·L−1, thyamine 100 mg·L−1, sacarose 3%, AIB 0.1 mg·L−1, zeatin 1 mg·L−1, imazapyr 150 nM, agar 1.4% and pH 4.0 for 15 days. Upon expiry of the period, the sprouts were separated and transferred into a sprout stretching mean (MAB) containing MS (Murashige and Skoog basal medium—Sigma M5519) added with inositol 100 mg·L−1, casein 300 mg·L−1, thyamine 100 mg·L−1, sacarose 3%, AIB 1 mg·L−1, giberetic acid (GA3) 1 mg·L−1, silver nitrate 5 µM, imazapyr 200 nM, agar 1.4% and pH 4.0, and kept under streaking at each 15-day period, until appearance of well structured and stretched explants of about 2-3 cm, that were transferred into a rooting mean containing MS (Murashige and Skoog basal medium—Sigma M5519) added with inositol 100 mg·L−1, casein 300 mg·L−1, thyamine 100 mg·L−1, sacarose 3%, AIB 2 mg·L−1, giberetic acid (GA3) 0.5 mg·L−1, silver nitrate 5 µM, agar 1.4% and pH 4.0. Plantules with about 3-4 cm and roots were acclimatized in vegetation house, in 700 mL glasses containing soil and vermiculite (1:1) with a plastic bag to keep moisture. Once acclimatized, the plants were transferred into a 8 L pot containing red latosols.

Example 4

Identification of Genetically Modified Castor-Oil Plants by Gus Histochemical Assay Tissues from the event TB14S-5D can be used in a histochemical assay to identify the event TB14S-5D from GUS protein expression in the x-gluc substrate according to Jefferson, R. A., Kavanagh, T. A. & Bevan, M. W. (GUS fusions: β-glucuronidase as a sensitive and versatile gene fusion marker in higher plants. *EMBO J.* 6, 3901-3907, 1987).

Figure 2:
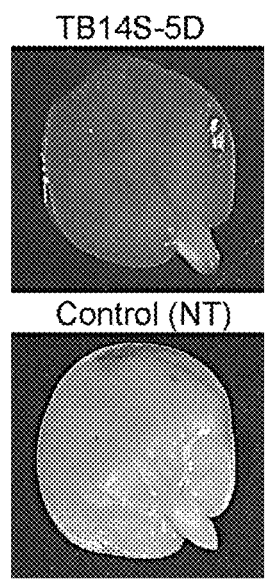
FIG. 2—Gus expression in the event TB14S-5D from histochemical assay. Non-transgenic embryons do not show gus expression.

As shown by the FIG. 2, the transgenic plant construct presents GUS gene, while the GUS marker was not expressed in the control plant.

Example 5

Identification of Genetically Modified Castor-Oil Plants by Southern Blot

It is possible to detect the event TB14S-5D by fixing the whole DNA of the event TB14S-5D in a membrane, and by hybridizing with a homologous probe the region Δricin corresponding to the region amplified with primers PSIUINTF (SEQ ID NO 19) and PSIUINTR (SEQ ID NO 20). Methodology according to [Lacorte, C., Vianna, G., Aragão, F. J. L. & Rech, E. L. Molecular Characterization of Genetically Manipulated Plants in Plant Cell Culture: Essential Methods (ed. Davey, M. R. & Anthony, P.) 261-279 (John Wiley & Sons, 2010)].

Figure 3:
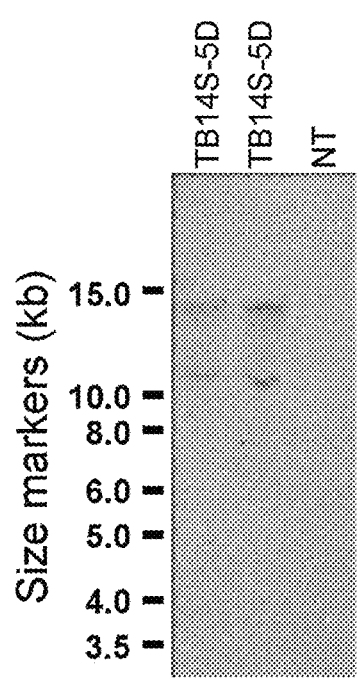
FIG. 3—The Southern blot assay shows the presence of transgenes representing Δricin (interference cassette) integrated inside the genome in two plants of the event TB14S-5D, while no signal is observed in non-transgenic plants (NT).
Figure 6:
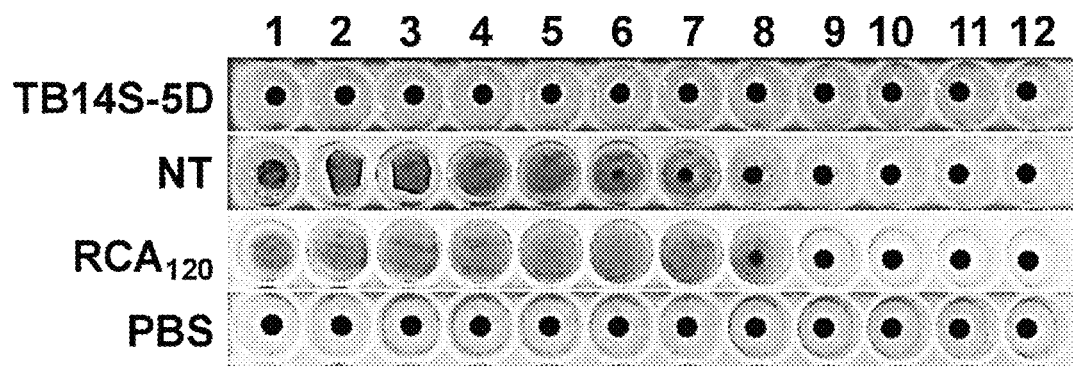
FIG. 6—The RCA120 silencing was observed in the hemagglutination assay. Seed proteins from the event TB14S-5D did not agglutinate red blood cells, as happened to the negative control (PBS) with the formation of a spot in the bottom of the plaque, while proteins of non-transgenic seeds (NT) agglutinated red blood cells, as happened to the positive control (RCA$_{120}$) with the formation of a diffuse bottom.
Figure 8:
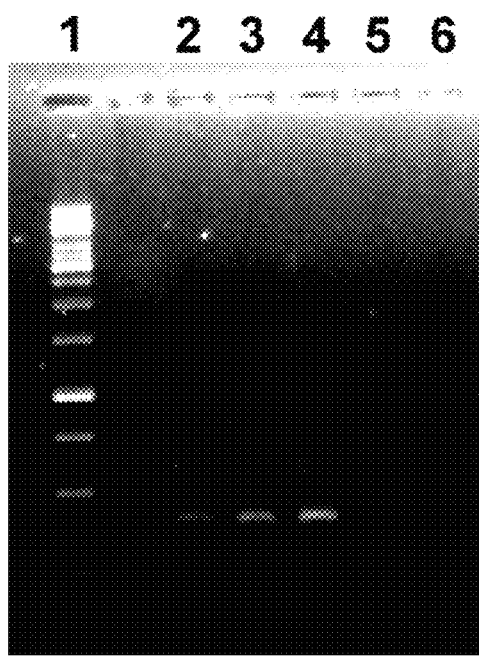
FIG. 8—PCR analysis showing the presence of fragments resulting from the amplification of a fragment corresponding to the SEQ. ID. No. 27, a specific marker for the event TB14S-5D. 1—1 kb marker (Tools); 2 to 4—GM plants of the event TB14S-5D; 5—pRicRNAi; vector; 6—Control (non-transgenic plant).
Figure 9:
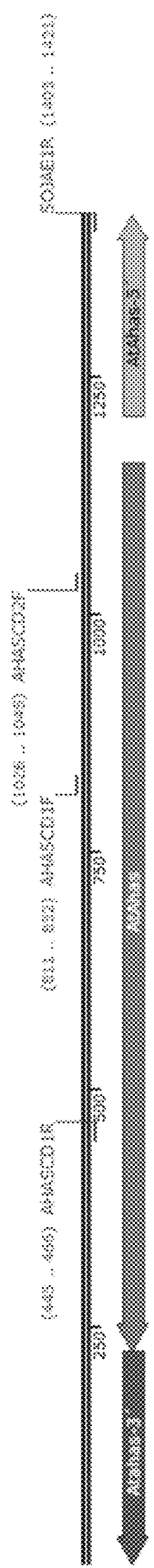
FIG. 9: A representation scheme of the region amplified by primers AHASCD2F (SEQ ID NO 25) and SOJAE1R (SEQ ID NO 26), the sequence of which is described in the SEQ. ID. No. 27.

The FIG. 3 shows the results from Southern blot for the identification of transgenic events.

Example 6

Identification of Genetically Modified Castor-Oil Plants by Northern Blot Analysis The analysis of RNAi from T1 seed endosperms allowed the identification of mRNAs of Ricin/RCA inside non-GM plants, as well as the identification of siRNAs in the endosperms of genetically modified T1 seeds.

Ricin silencing was detected in the event TB14S-5D by isolating the RNA and by hybridizing with a homologous probe the ricin region corresponding to the amplified 148 pb fragment by employing the pair of primers Ric149RNAiF (SEQ ID NO 23)/RcRinf: (SEQ ID NO 24). The methodology was implemented according to Aragão, F. J. L., Nogueira, E. O. P. L., Tinoco, M. L. P. & Faria, J. C. Molecular characterization of the first commercial transgenic common bean immune to the Bean golden mosaic virus. J. Biotechnol. 166, 42-50; 10.1016/j.jbiotec.2013.04.009, 2013).

The FIG. 4 shows the transgenic plants of the event identified by Northern blot.

Example 7

Identification of Genetically Modified Castor-Oil Plants by ELISA

It is possible to detect the ricin silencing in the event TB14S-5D by extracting whole proteins and by quantifying the amount of ricin in mature seeds of the event TB14S-5D by ELISA (Enzyme-Linked Immunosorbent Assay) de acordo com (Baldoni, A. B., Araújo, A. C. G., Carvalho, M. H., Gomes, A. C. M. M. & Aragão, F. J. L. Immunolocalization of ricin accumulation during castor bean (*Ricinus communis* L.) seed development. Int. J. Plant Biol. 1: and 12, 61-65, 2010).

ELISA was used to detect and quantify the amount of ricin in segregating seeds from the transgenic lineage TB14S-5D. As shown by the results, the wild-type (Non-GM) seeds presented 20 ng ricin/μg of whole protein, while the segregating seeds (that do not contain transgenes) presented statistically similar amounts of ricin, when compared to the control (non-transgenic plants). In contrast, ricin was not detectable by ELISA in transgenic seeds. Considering the cross-reaction between the antibody produced against ricin A channel and RCA120 due to their high identity, our results indicated that both ricin and RCA120 were silenced.

FIG. 5 shows the detection of ricin silencing in the event TB14S-5D. Ricin was detected in the endosperm of non-transgenic seeds and in the negative segregating seeds. Nevertheless, no ricin was detected in positive seeds from the event TB14S-5D.

Example 8

Hemagglutination Assay

RCA120 silencing in the event TB14S-5D was detected by red blood cell hemagglutination assay, through extraction of whole proteins of the event TB14S-5D and addition into blood solution under serial dilution, where the non-hemagglutination of red blood cells was observed.

Ricin is a lectin that has been described as weak hemagglutinine, while RCA120 presents a strong hemagglutinating activity. So, we performed an hemagglutination test with whole proteins isolated from the endosperm of both transgenic and non-transgenic castor-oil seeds. Strong hemagglutination was observed when isolated proteins of non-transgenic seeds were used at the 2.5 μg/μL concentration of whole protein, and even the 19 ng/μL concentration of whole protein was evident. In contrast, no hemagglutination activity was detected with proteins isolated from transgenic seeds, not even at the highest protein concentration (about 131-fold more concentrated). Moreover, the agglutination activity was not observed in ox blood cells incubated with PBS (white), while the purified RCA120 presented strong hemagglutinating activity event at a 0.39 ng/μL concentration. In addition to the absence of transcripts, the ricin and RCA120 proteins were not detected in the endosperms of T1 seeds from the TB14S-5D, thus confirming the efficient Ricin and RCA120 silencing.

FIG. 6 shows the result from a hemagglutination assay performed with proteins from seeds of the event TB14S-5D and with control group: the proteins from seeds of the event TB14S-5D did not agglutinate red blood cells as happened to the negative control (PBS) with the formation of a spot on the bottom of the plaque, while proteins from non-transgenic seeds agglutinated red blood cells as happened to the positive control (RCA120), with the formation of a diffuse bottom.

Example 9

Identification of Genetically Modified Castor-Oil Plants by PCR

It is possible to detect the event TB14S-5D by PCR by using the pairs of primers PSIUINTF (SEQ ID NO 19) with PSIUINTR (SEQ ID NO 20) and AHASCD2F (SEQ ID NO 25) with SOJAE1R (SEQ ID NO 26). Methodology implemented according to Lacorte, C., Vianna, G., Aragão, F. J. L. & Rech, E. L. Molecular Characterization of Genetically Manipulated Plants in Plant Cell Culture: Essential Methods (ed. Davey, M. R. & Anthony, P.) 261-279 (John Wiley & Sons, 2010). The FIG. 9 presents a scheme showing the region amplified by the primers AHASCD2F and SOJAE1R.

The FIGS. 7 and 8 show that the transgenic plants of the event were detected by the relevant primers. In the FIG. 8, it is possible to identify the presence of 396 pb strand referring to the SEQ. ID. No. 27, that is a specific marker to the event TB14S-5D.

Example 10

Cell Feasibility Study

Epithelial cells from mouse gut (IEC-6) were incubated for 24 hours with total proteins isolated from endosperm of both transgenic and non-transgenic seeds. The feasibility of the cells exposed to proteins isolated from non-GM plants containing 1 or 10 ng ricin/mL was reduced to 53% and 16% respectively. Nevertheless, cells exposed to the corresponding amount of proteins from transgenic seed kept their feasibility at 97% (at 0.5 μg total protein/mL) and at 78% at the highest protein concentration (50 μg total protein/mL). There was no statistic difference between the feasibility percentages of 97% and 78%, and such results were corroborated by the fact that the protein synthesis was inhibited within a range from 40% to 90% in cells cultured for 5 hours with proteins from non-transgenic seeds containing 0.1 and 1 ng ricin/mL respectively. Nevertheless, no inhibition was observed in cells cultured in the presence of the corresponding amount of proteins isolated from transgenic seeds, not even at the highest total protein concentration. Accordingly, we demonstrated that the seeds from GM plants were not toxic to the culture of epithelial cells from mouse gut.

Example 11

Cell Survival Test

Mice (Swiss Webster) were treated by intraperitoneal administration with endosperm from castor-oil plant seeds to the measurement of ricin in the lethal challenge test. We performed the ricin challenge by injecting into mice whole proteins isolated from the event TB14S-5D, as well as from non-transgenic seeds. As expected, all the animals that underwent the intraperitoneal injection with 20 μg wild-type see proteins/g of body weight (552 μg ricin/kg of body weight) died within the first 24-hour period. Nevertheless, animals injected with the corresponding amounts of whole proteins isolated from seeds of the event TB14S-5D survived without visible symptoms of intoxication by ricin (diarrhea, weakness, loss of appetite, black stools, and loss of weight). As a matter of fact, a remarkably reduced glycaemia level was observed among animals injected with proteins from non-transgenic seeds. Nevertheless, there was no significant alteration in the glycaemia of animals injected with proteins from transgenic seeds for a 60 hour-period. The animals were monitored for an additional 7-day period, and no death was recorded in the group of mice injected with proteins from the event TB14S-5D. In the in vivo toxicity test with whole proteins isolated from seeds of the event TB14S-5D, not even an amount 15 to 230-fold of amounts of DL50 presented toxic effects for mice. According to these results, we estimated that mice could consume GM castor bean cake in an amount up to 52% of their body weight without presenting acute intoxication. Generally, the daily consumption of protein sources by cows, sheeps and goats only represents 1 to 2% of their body weight.

DEPOSIT INFORMATION

A deposit of *Ricinus communis* seed comprising Event TB 14S-5D has been made and accepted under the Budapest Treaty with the National Collection of Industrial, Food and Marine Bacteria Ltd. (NCIMB Ltd.), Wellsheads Place, Aberdeen, Dyce, AB21 7 GB, Scotland. The date of deposit was Oct. 10, 2024. The NCIMB Accession No. is 44438.

The invention claimed is:

1. A *Ricinus communis* plant comprising event TB14S-5D, wherein seed comprising said event has been deposited under NCIMB Accession No: 44438, and wherein said event TB14S-5D comprises:

a promoter sequence comprising a nucleotide sequence of SEQ ID NO: 4;

a first dsRNA coding sequence comprising a nucleotide sequence of SEQ ID NO: 12;

a second dsRNA coding sequence comprising a nucleotide sequence of SEQ ID NO: 13;

a spacing sequence between the first and the second dsRNA coding sequence comprising a nucleotide sequence of SEQ ID NO: 5;

a termination signal sequence comprising a nucleotide sequence of SEQ ID NO: 6;

a marker gene comprising a promoter sequence comprising a nucleotide sequence of SEQ ID NO: 7, a coding sequence comprising a nucleotide sequence of SEQ ID NO: 8, and a termination signal sequence comprising a nucleotide sequence of SEQ ID NO: 9; and a selection gene comprising a nucleotide sequence of SEQ ID NO:1, a coding region comprising a nucleotide sequence of SEQ ID NO:2 and a termination signal comprising a nucleotide sequence of SEQ ID NO: 3.

2. A *Ricinus communis* seed or propagative part from the *Ricinus communis* plant of claim 1, wherein the seed or propagative part comprises event TB14S-5D.

* * * * *